US007071379B2

(12) United States Patent
Fischer et al.

(10) Patent No.: US 7,071,379 B2
(45) Date of Patent: Jul. 4, 2006

(54) METHODS FOR ALTERING ORGAN MASS IN PLANTS

(75) Inventors: Robert L. Fischer, El Cerrito, CA (US); Yukiko Mizukami, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/059,911

(22) Filed: Jan. 28, 2002

(65) Prior Publication Data

US 2003/0159180 A1    Aug. 21, 2003

(51) Int. Cl.
*C12N 15/82*    (2006.01)
(52) U.S. Cl. .................... 800/290; 435/320.1
(58) Field of Classification Search ........... 800/290; 435/320.1, 468
See application file for complete search history.

(56) References Cited

U.S. PATENT DOCUMENTS

| 5,110,732 | A  | * | 5/1992  | Benfey et al. | ............... | 800/287 |
| 6,559,357 | B1 | * | 5/2003  | Fischer et al. | ............... | 800/290 |
| 6,639,128 | B1 | * | 10/2003 | Fischer et al. | ............... | 800/290 |

OTHER PUBLICATIONS

Klucher et al. The *Aintegumenta* gene of Arabidopsis required for ovule and female gametophyte development is related to the floral homeotic gene APETALA2, The Plant Cell, vol. 8, pp. 137-153, Feb. 1996.*
Elliott et al. *Aintegumenta*, an APETALA2-like gene of Arabidopsis with pleiotropic roles in ovule development and floral organ growth. The Plant Cell, vol. 8, pp. 155-168, Feb. 1996.*
Krizek BA. *Aintegumenta* utilizes a mode of DNA recognition distinct from that used by proteins containing a single AP2 domain.Nucleic Acids Res. Apr. 1, 2003; 31(7): 1859-68.*
Nole-Wilson S, Krizek BA. DNA binding properties of the Arabidopsis floral development protein *Aintegumenta*. Nucleic Acids Res. Nov. 1, 2000: 28(21); 4076-82.*
SPTREMBL Accession No. Q42462, Nov. 1, 1996, ovule development protein *Aintegumenta* from Arabidopsis thaliana.*
Krizek B.A. *Aintegumenta* utilizes a mode of DNA recognition distinct from that used by proteins containing a single AP2 domain. Nucleic Acids Res. Apr. 1, 2003;31(7):1859-68.*
Klucher, K.; Database PIR, Accession No. S71365, Gene Sequence, Oct. 28, 1996.
Krizek, Beth A.; "Ectopic Expression of *Aintegumenta* in Arabidopsis Plants Results in Increased Growth of Floral Organs"; *Developmental Genetics* 1999, vol. 25, pp. 224-236.
Mizukami, Yukiko et al.; "Plant organ size control: *Aintegumenta* regulates growth and cell numbers during organogenesis"; *PNAS* 2000, vol. 97 No. 2 pp. 942-947.

* cited by examiner

*Primary Examiner*—Cynthia Collins
(74) *Attorney, Agent, or Firm*—Townsend and Townsend and Crew LLP

(57) ABSTRACT

The invention provides methods of altering organ mass, controlling fertility and enhancing asexual reproduction in plants through the modulation of plant growth and cell proliferation. The methods involve producing transgenic plants comprising a recombinant expression cassette containing a modified ANT nucleic acid linked to a plant promoter.

24 Claims, No Drawings

SEQUENCE LISTING

```
<160> NUMBER OF SEQ ID NOS: 42

<210> SEQ ID NO 1
<211> LENGTH: 2148
<212> TYPE: DNA
<213> ORGANISM: Arabidopsis thaliana
<220> FEATURE:
<223> OTHER INFORMATION: AINTEGUMENTA (ANT) cDNA
<220> FEATURE:
<221> NAME/KEY: CDS
<222> LOCATION: (269)..(1936)
<223> OTHER INFORMATION: Arabidopsis AINTEGUMENTA (ANT)

<400> SEQUENCE: 1
agatcccaac ggattcaaac agcaaatttg tgctttgctc ttctctctta ttataatatc      60
ctctcaaaaa ccctctccta tatcctccta aagccccccct tccttgtttc tctaccgcaa    120
caaagaaaaa acaaaagttt gagaaaaatg gtgtgttcgt tgtgtaacca atgattgggt     180
tttagcttac tacttcgaga gattataaga aagaaagagt gaagatacat tatagaaaga    240
agagaagcag aaaccaaaaa aagaaaccat gaagtctttt tgtgataatg atgataataa    300
tcatagcaac acgactaatt tgttagggtt ctcattgtct tcaaatatga tgaaaatggg    360
aggtagagga ggtagagaag ctatttactc atcttcaact tcttcagctg caacttcttc    420
ttcttctgtt ccacctcaac ttgttgttgg tgacaacact agcaactttg gtgtttgcta    480
tggatctaac ccaaatggag gaatctattc tcacatgtct gtgatgccac tcagatctga    540
```

```
                                                              -continued tggttctctt tgcttaatgg aagctctcaa cagatcttct cactcgaatc accatcaaga     600
ttcatctcca aggtggagg atttctttgg gacccatcac aacaacacaa gtcacaaaga     660
agccatggat cttagcttag atagtttatt ctacaacacc actcatgagc caacacgac     720 tacaaacttt caagagttct ttagcttccc tcaaaccaga aaccatgagg aagaaactag    780
aaattacggg aatgacccta gtttgacaca tggagggtct tttaatgtag ggtatatgg    840 ggaatttcaa cagtcactga gcttatccat gagccctggg tcacaatcta gctgcatcac    900
tggctctcac caccaccaac aaaaccaaaa ccaaaaccac aaagccaaa accaccagca    960 gatctctgaa gctcttgtgg agacaagcgt tgggtttgag acgacgacaa tggcggctgc    1020
gaagaagaag aggggacaag aggatgttgt agttgttggt cagaaacaga ttgttcatag    1080
aaaatctatc gatacttttg gacaacgaac ttctcaatac cgaggcgtta caagacatag    1140
atggactggt agatatgaag ctcatctatg ggacaatagt ttcaagaagg aaggtcacag    1200
tagaaaagga agacaagttt atctgggagg ttatgatatg gaggagaaag ctgctcgagc    1260
atatgatctt gctgcactca gtactgggg tccctctact cacaccaatt tctctgcgga    1320
gaattatcag aaagagattg aagacatgaa gaacatgact agacaagaat atgttgcaca    1380
tttgagaagg aagagcagtg gtttctctag gggtgcttcc atctatagag gagtcacaag    1440
acatcaccag catggaaggt ggcaagcacg gattggtaga gtcgctggaa acaaagatct    1500
ctaccttgga acttttggaa cccaagaaga agctgcagaa gcttacgatg tagcagcaat    1560
taagttccgt ggcacaaatg ctgtgactaa ctttgatatc acgaggtacg atgttgatcg    1620
tatcatgtct agtaacacac tcttgtctgg agagttagcg cgaaggaaca acaacagcat    1680
tgtcgtcagg aatactgaag accaaaccgc tctaaatgct gttgtggaag gtggttccaa    1740
caaagaagtc agtactcccg agagactctt gagttttccg gcgattttcg cgttgcctca    1800
agttaatcaa aagatgttcg gatcaaatat gggcggaaat atgagtcctt ggacatcaaa    1860
ccctaatgct gagcttaaga ccgtcgctct tactttgcct cagatgccgg ttttcgctgc    1920
ttgggctgat tcttgatcaa cttcaatgac taactctggt tttcttggtt tagttgctaa    1980
gtgttttggt ttatctccgg ttttatccgg tttgaactac aattcggttt agtttcgtcg    2040
gtataaatag tatttgctta ggagcggtat atgtttcttt tgagtagtat tcatgtgaaa    2100
cagaatgaat ctctctataa catattattt taatgaatct cctttgct                 2148

<210> SEQ ID NO 2
<211> LENGTH: 555
<212> TYPE: PRT
<213> ORGANISM: Arabidopsis thaliana
<220> FEATURE:
<223> OTHER INFORMATION: Arabidopsis AINTEGUMENTA (ANT)

<400> SEQUENCE: 2

Met Lys Ser Phe Cys Asp Asn Asp Asp Asn Asn His Ser Asn Thr Thr
  1               5                  10                  15

Asn Leu Leu Gly Phe Ser Leu Ser Ser Asn Met Met Lys Met Gly Gly
             20                  25                  30

Arg Gly Gly Arg Glu Ala Ile Tyr Ser Ser Ser Thr Ser Ser Ala Ala
         35                  40                  45

Thr Ser Ser Ser Ser Val Pro Pro Gln Leu Val Val Gly Asp Asn Thr
     50                  55                  60

Ser Asn Phe Gly Val Cys Tyr Gly Ser Asn Pro Asn Gly Gly Ile Tyr
 65                  70                  75                  80
```

-continued

```
Ser His Met Ser Val Met Pro Leu Arg Ser Asp Gly Ser Leu Cys Leu
                85                  90                  95

Met Glu Ala Leu Asn Arg Ser His Ser Asn His His Gln Asp Ser
            100                 105                 110

Ser Pro Lys Val Glu Asp Phe Phe Gly Thr His His Asn Asn Thr Ser
            115                 120                 125

His Lys Glu Ala Met Asp Leu Ser Leu Asp Ser Leu Phe Tyr Asn Thr
        130                 135                 140

Thr His Glu Pro Asn Thr Thr Thr Asn Phe Gln Glu Phe Phe Ser Phe
145                 150                 155                 160

Pro Gln Thr Arg Asn His Glu Glu Thr Arg Asn Tyr Gly Asn Asp
                165                 170                 175

Pro Ser Leu Thr His Gly Gly Ser Phe Asn Val Gly Val Tyr Gly Glu
            180                 185                 190

Phe Gln Gln Ser Leu Ser Leu Ser Met Ser Pro Gly Ser Gln Ser Ser
            195                 200                 205

Cys Ile Thr Gly Ser His His His Gln Gln Asn Gln Asn Gln Asn His
        210                 215                 220

Gln Ser Gln Asn His Gln Gln Ile Ser Glu Ala Leu Val Glu Thr Ser
225                 230                 235                 240

Val Gly Phe Glu Thr Thr Thr Met Ala Ala Ala Lys Lys Lys Arg Gly
                245                 250                 255

Gln Glu Asp Val Val Val Val Gly Gln Lys Gln Ile Val His Arg Lys
            260                 265                 270

Ser Ile Asp Thr Phe Gly Gln Arg Thr Ser Gln Tyr Arg Gly Val Thr
        275                 280                 285

Arg His Arg Trp Thr Gly Arg Tyr Glu Ala His Leu Trp Asp Asn Ser
        290                 295                 300

Phe Lys Lys Glu Gly His Ser Arg Lys Gly Arg Gln Val Tyr Leu Gly
305                 310                 315                 320

Gly Tyr Asp Met Glu Glu Lys Ala Ala Arg Ala Tyr Asp Leu Ala Ala
                325                 330                 335

Leu Lys Tyr Trp Gly Pro Ser Thr His Thr Asn Phe Ser Ala Glu Asn
            340                 345                 350

Tyr Gln Lys Glu Ile Glu Asp Met Lys Asn Met Thr Arg Gln Glu Tyr
            355                 360                 365

Val Ala His Leu Arg Arg Lys Ser Ser Gly Phe Ser Arg Gly Ala Ser
        370                 375                 380

Ile Tyr Arg Gly Val Thr Arg His His Gln His Gly Arg Trp Gln Ala
385                 390                 395                 400

Arg Ile Gly Arg Val Ala Gly Asn Lys Asp Leu Tyr Leu Gly Thr Phe
                405                 410                 415

Gly Thr Gln Glu Glu Ala Ala Glu Ala Tyr Asp Val Ala Ala Ile Lys
            420                 425                 430

Phe Arg Gly Thr Asn Ala Val Thr Asn Phe Asp Ile Thr Arg Tyr Asp
        435                 440                 445

Val Asp Arg Ile Met Ser Ser Asn Thr Leu Leu Ser Gly Glu Leu Ala
450                 455                 460

Arg Arg Asn Asn Asn Ser Ile Val Val Arg Asn Thr Glu Asp Gln Thr
465                 470                 475                 480

Ala Leu Asn Ala Val Val Glu Gly Gly Ser Asn Lys Glu Val Ser Thr
                485                 490                 495
```

```
             Pro Glu Arg Leu Leu Ser Phe Pro Ala Ile Phe Ala Leu Pro Gln Val
                     500                 505                 510

Asn Gln Lys Met Phe Gly Ser Asn Met Gly Gly Asn Met Ser Pro Trp
                     515                 520                 525

Thr Ser Asn Pro Asn Ala Glu Leu Lys Thr Val Ala Leu Thr Leu Pro
                     530                 535                 540

Gln Met Pro Val Phe Ala Ala Trp Ala Asp Ser
             545                 550                 555

<210> SEQ ID NO 3
<211> LENGTH: 4228
<212> TYPE: DNA
<213> ORGANISM: Arabidopsis thaliana
<220> FEATURE:
<223> OTHER INFORMATION: AINTEGUMENTA (ANT) promoter, 5'-upstream
      sequence of ANT gene

<400> SEQUENCE: 3
gtcgactcta ggcctcactg gcctaatacg actcactata gggagctcga ggatccttta      60
gttagaaaaa actttctttg tacgtgtgtg tgtgttttt aagttcaatt ataactagtc     120
acatgtgata tcacaatata tatattgaaa ttggaattat tcatattaat gagttagcat     180
taatatatat acgctgacat taccaaccaa atgtttctgc ttttatggat agttctatat     240
gttgcacttg attatagata ctatataaaa ctgggtttat ttaaaatccg tacccataac     300
aaaagtggac caaaacgaga tccatggttt tgtgtttact tgttggtta accagataat     360 atgattatgg aagattaaat ctttactaaa ttataaaata atttggaaaa acaaacttaa     420
atatgttgag tgtcttcagt gctcactgtt caagaataat ctcgtgttat cctacttgaa     480
ctagaagttg atatacataa acacgtgaat attttaacga ccgtacataa acacatgtat     540
cgatcaaata caaattatta tgagactaga atccaagatg aggatgactc tagcagaata     600
tacacagcta agaatttgta caagagagtc gaaaaataga ttctaatcat ttaaaaaga     660 tatggatttc agttacggat tgatattacc attacgcagt agtacataca cataattttt     720 tgttttgtt ttaccgataa tagaatgaaa atgttgtgtt aaaatatttg gttttactaa     780
aactcgtttt atgttaacta tataatgtct ttccgcatgt aaattgaaac aaaactgtaa     840
tacaaattat gttaagccat tgcaattaaa aaatccacgg gtagtaaatc ctcagaagat     900
tatgttaagt ctacaaattt ctctctttaga ttagtaaggt ttgagacaaa attatgtata     960
ccttgcaggg gtataaaggt cactgcatag tcagactcag catgaagcca agagtcgtc    1020 tctgtcctaa agatatctac agctgcttcg cctgtgaata gagaagaaat tgaatgatga    1080
gagatcccat ctagcgtttc acgtttgcgt tctccgtcgc aactttggcg gttgttgact    1140
ttttttctta tgtcgttgtt tgactaattt tctcagagtg agagtgtaat caagaaaact    1200
aatattcgaa agaaagaaa aaaaaggcaa gaaaactatt gtcgaaaaga cataaatgac    1260
actaaaattg gattattaaa aatggtatat atgtttggtg gaatttataa tcattaccaa    1320
aatcaaagga aggagagagg gacctcttcg tgcttatgat ttccctccta acaactgct    1380 cccactatcc ttttttactt ccaacaaaat cattcacacg agaaaatctg tctcgtgatc    1440
actttcatgc aaaattaaac taaatttttg tatttttgt caagttcttg ctgttttaag    1500
tcgattattt ggtaatacta tatgtgtgga tatacacatc caagctaatc aataattgat    1560
ctccttctgc ttatcaataa attacaccac attagctaat caagctaata aattacacca    1620
cattctctta tcaattttta tatggtataa ataaacaac cgactatagg ctacagagtt    1680
```

```
ggtattaagg cattattgcc ttctagtcga aggaattttt ttgttatgat aacactcgtg   1740
ggaaaaaaat ccagcctaat atgctcattt aaaggataat tgatttaaat gctttaatca   1800
ttaaaataaa aggtttttgc ttttaaaggt taccaccgct taattcatca ttaggagaat   1860
attaactttg atcgaaattc caaaatactt ttttaacaca taagaaaatt ttcagcattt   1920
ttaaataaag ggtacattta ttgggttcaa taaatatgtt tccacgtaaa gtttggaggt   1980
ttaaccacat gaatgttttt tgatttaaaa aacacataaa ttttctagta attacacatt   2040
tttaaccgtc catccagatt gtaataagtg acaaatctga aaacattttt tttttcttg    2100 aatcttgttt aaattctctc tgctgcatac ttgcaggcat ttgaccaacg actatacata   2160
ttgaaagcaa aatatccacc agggatgata gggttagatc ccacattcaa tatcttttgt   2220
ctttgttatt tatgaaaaac aaatatttat caggaaaaaa acgttttcttc tctagtggta   2280 taagtataag ataataacaa aatttaatac ttagttaatg tatttactat cttcaaactt   2340
accatccttc aacattaata ttgatcaatt tttattttt ttactaaact acttccacta     2400
aaaaaatgca aagaagaga tatatattta agtcaaagta attaaagatg gatgggtgat    2460
tcttcagcaa aacggcgccg tagaggtgtc ttatcctaca ttacagctgg gttgtggcag   2520
acatcatagg gcctacgtat atttgagctt tactgtacgt aaagctttaa catatctagt   2580
tagttctcac tgtacaaaca aaacaaaatc caattcgtaa catatataca aatactacta   2640
gtactagatt acgctacgta tacatcgctt tttcgcaaat ttctaaacta atctatacaa   2700
caaacttgaa tgtttgtttt gtaatttatc ttaaaccaaa gttttgaatt gtgcattggg   2760
agctacactc tagtccccctt ttttccccaa ataatctcc ttacatcgac cggttaaagt    2820
atttaaacca acaaattta atttgttgct gaaggtacaa acatgtcaca tatatagaga    2880
cagcatcgtt tatacaaata atgttcgatg ttattggaaa tcaaatataa atacgagtag   2940
cgactcactt ggtttaatag tttggaagat aatgaaataa aaagatgaat tcaaaggata   3000
cagagctata tatgtcgggt catttagagc cgtgaccaaa agtttcgtcg taatttctac   3060
ggtcggtcat aagaaatttt ggacttttct tcacccttt atgaacttct gtatagtttt    3120
tgtcggatta tatatttgta ttcgtatatt ttttgtttct aataatgata cgtaaattca   3180
cgataagaaa gacttctttt tatttaattt gatttaaaac ttttgttttt ggaaatgact   3240
catacacaag gttaaagttt gatggtatcc aatttacaaa aatgtttcga gagtgcgttc   3300
gagtgtccta ccaccatcgt accaactcgt atgggtttat tattaggttt ttttcttctt   3360
tttccaatgt ctttataatt gaaccactct aaatttcttt ttttaaatta ggttaagaat   3420
cttgaatttt ctgttgattt taaccaagg ttttcaattc ttcttagcac aaaaaaaaaa    3480
aaaaggtttt caattattaa agaatctaaa tttttttgagt tcaagagttt aatgatagct   3540
gaaaagttat gaatgattgc aagtttgcaa cagaatggtc gatgtagtac atatcaaaaa   3600
catgcatcaa aataaatatt cgtgcttagc aagagaaacg attgaaataa acagaacaat   3660
cgttaaccac ttaaaaatct tagaataatt ttgtagtgat aattttctgt aagagagagg   3720
tatcatatct tacaaaaaaa aactcatttc agataaaata atgttgtcca atcgttacca   3780
agtatgtttt tgctgtcatc agttgtattg taactcgtct cttagccata tagttctaag   3840
ttttaaatgt tttcaaagac tttacaaaaa taaaataata ataaggtgga atttgtaggg   3900
ctaaaagcga aaaataaaaa taaaataaaa gtaaagaaac gtctttctca ataagaacac   3960
agatcccaac ggattcaaac agcaaatttg tgctttgctc ttctctctta ttataatatc   4020
ctctcaaaaa ccctctccta tatcctccta aagcccccct tccttgtttc tctaccgcaa   4080
```

-continued

| | |
|---|---|
| caaagaaaaa acaaaagttt gagaaaaatg gtgtgttcgt tgtgtaacca atgattgggt | 4140 |
| tttagcttac tacttcgaga gattataaga aagaaagagt gaagatacat tatagaaaga | 4200 |
| agagaagcag aaaccaaaaa aagaaacc | 4228 |

<210> SEQ ID NO 4
<211> LENGTH: 1738
<212> TYPE: DNA
<213> ORGANISM: Brassica napus
<220> FEATURE:
<223> OTHER INFORMATION: Canola AINTEGUMENTA (ANT) ortholog partial cDNA
      including coding region
<220> FEATURE:
<221> NAME/KEY: CDS
<222> LOCATION: (1)..(1647)
<223> OTHER INFORMATION: Canola AINTEGUMENTA (ANT)

<400> SEQUENCE: 4

| | |
|---|---|
| atgaagtctt tttgtgataa tgatgatagt aatacgacta atttgctagg gttctcgttg | 60 |
| tcttcaaata tgttgaaaat gggtggtgga gaagctcttt actcatcttc gtcgtcttca | 120 |
| gttgcaactt cttctgttcc accacagctt gttgttggcg acaacagtag caactatgga | 180 |
| gtttgctacg gttctaactt agcagctagg gaaatgtatt ctcaaatgtc tgtgatgccc | 240 |
| ctcagatctg acggttctct ttgcttaatg gaagctctca acagatcttc tcactcgaat | 300 |
| aatcatcacc atagtcaagt tcatctccca aagatggaag atttctttgg gacccatcat | 360 |
| cacaacacaa gtcacaaaga agccatggat cttagcttag atagtttatt ctacaatacc | 420 |
| actcatgcgc aaacaacaa caccaacttt caagagttct ttagcttccc tcaaactaga | 480 |
| aaccaccatg aggaagaaac aagaaactac gagaatgacc ctggtttgac acatggagga | 540 |
| gggtctttta atgtaggggt atatggggaa tttcaacagt cactgagctt gtccatgagc | 600 |
| cctgggtcac aatctagctg catcactgcc tctcatcacc accaaaaacca aactcaaaac | 660 |
| caccagcaga tctctgaagc tttggtcgag acaagtgctg gatttgagac aacaacaatg | 720 |
| gcggctgctg ctgcaaagaa gaagagagga caagaagttg tcgttggaca gaaacagatt | 780 |
| gttcatagaa aatctattga tacttttgga caacgaactt cgcaataccg aggcgttaca | 840 |
| agacatagat ggactggtag gtatgaagct catctctatg ggacaatagtttt caagaaggaa | 900 |
| ggtcatagca gaaaggaag acaagtttat ctgggggggtt atgatatgga ggagaaagct | 960 |
| gctcgagcat atgatcttgc tgcactcaag tactgggggtc cctctactca cactaatttc | 1020 |
| tctgtggaga attatcagaa agagattgat gacatgaaga acatgactcg acaagaatat | 1080 |
| gttgctcact tgagaagaaa aaccagtggt ttctctaggg gtgcttccat ctatagagga | 1140 |
| gtcaccagac atcaccagca tggaaggtgg caagctcgga tcggtagagt cgctggaaac | 1200 |
| aaagatctct accttggaac tttcggaact caagaagaag cggcggaagc ctatgatgta | 1260 |
| gcagctatca agttccgtgg cacaaacgcg gtgactaact tgacataac aaggtacgat | 1320 |
| gttgatcgca taatggctag taacactctc ttgtctggag agatggctcg aaggaacagc | 1380 |
| aacagcatcg tggtccgcaa cattagcgac gaggaagccg ctttaaccgc tgtcgtgaac | 1440 |
| ggtggttcca ataaggaagt gggtagcccg agagggtttt gagttttcc gacgatattt | 1500 |
| gcgttgcctc aagttggtcc gaagatgttc ggagcaaatg tggtcggaaa tatgagttct | 1560 |
| tggactacga accctaatgc tgatctcaag accgtttctc ttactctgcc gcagatgccg | 1620 |
| gttttcgctg cgtgggctga ttcttaattc aatctaatgg ctaactctgg ttttcttggt | 1680 |
| ttagggtcca agtgtttaag tttatctccg ggtttatccg gtttgaacta caattcgg | 1738 |

<210> SEQ ID NO 5
<211> LENGTH: 548
<212> TYPE: PRT
<213> ORGANISM: Brassica napus
<220> FEATURE:
<223> OTHER INFORMATION: Canola AINTEGUMENTA (ANT)

<400> SEQUENCE: 5

```
Met Lys Ser Phe Cys Asp Asn Asp Asp Ser Asn Thr Thr Asn Leu Leu
  1               5                  10                  15

Gly Phe Ser Leu Ser Ser Asn Met Leu Lys Met Gly Gly Gly Glu Ala
             20                  25                  30

Leu Tyr Ser Ser Ser Ser Ser Val Ala Thr Ser Ser Val Pro Pro
         35                  40                  45

Gln Leu Val Val Gly Asp Asn Ser Ser Asn Tyr Gly Val Cys Tyr Gly
     50                  55                  60

Ser Asn Leu Ala Ala Arg Glu Met Tyr Ser Gln Met Ser Val Met Pro
 65                  70                  75                  80

Leu Arg Ser Asp Gly Ser Leu Cys Leu Met Glu Ala Leu Asn Arg Ser
                 85                  90                  95

Ser His Ser Asn Asn His His His Ser Gln Val Ser Ser Pro Lys Met
            100                 105                 110

Glu Asp Phe Phe Gly Thr His His Asn Thr Ser His Lys Glu Ala
        115                 120                 125

Met Asp Leu Ser Leu Asp Ser Leu Phe Tyr Asn Thr Thr His Ala Pro
130                 135                 140

Asn Asn Asn Thr Asn Phe Gln Glu Phe Ser Phe Pro Gln Thr Arg
145                 150                 155                 160

Asn His His Glu Glu Glu Thr Arg Asn Tyr Glu Asn Asp Pro Gly Leu
                165                 170                 175

Thr His Gly Gly Gly Ser Phe Asn Val Gly Val Tyr Gly Glu Phe Gln
            180                 185                 190

Gln Ser Leu Ser Leu Ser Met Ser Pro Gly Ser Gln Ser Ser Cys Ile
        195                 200                 205

Thr Ala Ser His His His Gln Asn Gln Thr Gln Asn His Gln Gln Ile
210                 215                 220

Ser Glu Ala Leu Val Glu Thr Ser Ala Gly Phe Glu Thr Thr Thr Met
225                 230                 235                 240

Ala Ala Ala Ala Ala Lys Lys Lys Arg Gly Gln Glu Val Val Gly
                245                 250                 255

Gln Lys Gln Ile Val His Arg Lys Ser Ile Asp Thr Phe Gly Gln Arg
            260                 265                 270

Thr Ser Gln Tyr Arg Gly Val Thr Arg His Arg Trp Thr Gly Arg Tyr
        275                 280                 285

Glu Ala His Leu Trp Asp Asn Ser Phe Lys Lys Glu Gly His Ser Arg
    290                 295                 300

Lys Gly Arg Gln Val Tyr Leu Gly Gly Tyr Asp Met Glu Glu Lys Ala
305                 310                 315                 320

Ala Arg Ala Tyr Asp Leu Ala Ala Leu Lys Tyr Trp Gly Pro Ser Thr
                325                 330                 335

His Thr Asn Phe Ser Val Glu Asn Tyr Gln Lys Glu Ile Asp Asp Met
            340                 345                 350

Lys Asn Met Thr Arg Gln Glu Tyr Val Ala His Leu Arg Arg Lys Thr
        355                 360                 365
```

```
Ser Gly Phe Ser Arg Gly Ala Ser Ile Tyr Arg Gly Val Thr Arg His
        370                 375                 380

His Gln His Gly Arg Trp Gln Ala Arg Ile Gly Arg Val Ala Gly Asn
385                 390                 395                 400

Lys Asp Leu Tyr Leu Gly Thr Phe Gly Thr Gln Glu Glu Ala Glu
            405                 410                 415

Ala Tyr Asp Val Ala Ala Ile Lys Phe Arg Gly Thr Asn Ala Val Thr
            420                 425                 430

Asn Phe Asp Ile Thr Arg Tyr Asp Val Asp Arg Ile Met Ala Ser Asn
            435                 440                 445

Thr Leu Leu Ser Gly Glu Met Ala Arg Arg Asn Ser Asn Ser Ile Val
    450                 455                 460

Val Arg Asn Ile Ser Asp Glu Glu Ala Ala Leu Thr Ala Val Val Asn
465                 470                 475                 480

Gly Gly Ser Asn Lys Glu Val Gly Ser Pro Glu Arg Val Leu Ser Phe
                485                 490                 495

Pro Thr Ile Phe Ala Leu Pro Gln Val Gly Pro Lys Met Phe Gly Ala
            500                 505                 510

Asn Val Gly Asn Met Ser Ser Trp Thr Thr Asn Pro Asn Ala Asp
    515                 520                 525

Leu Lys Thr Val Ser Leu Thr Leu Pro Gln Met Pro Val Phe Ala Ala
    530                 535                 540

Trp Ala Asp Ser
545

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence:consensus
      ANT polynucleotide sequence-1

<400> SEQUENCE: 6
atgaagtctt tttgtgataa tgatgatagt aat                               33

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence:consensus
      ANT polynucleotide sequence-2

<400> SEQUENCE: 7
acgactaatt tgttagggtt ctcattgtct tcaaatatg                         39

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence:consensus
      ANT polynucleotide sequence-3

<400> SEQUENCE: 8
agaatcagcc caagcagcga aaaccggcat ctgcggca                          38

<210> SEQ ID NO 9
<211> LENGTH: 473
```

```
<212> TYPE: PRT
<213> ORGANISM: Artificial Sequence
<220> FEATURE:
<223> OTHER INFORMATION: Description of Artificial Sequence:structurally
      altered ANT protein ANTDN1

<400> SEQUENCE: 9
```

| | | | | | | | | | | | | | | | |
|---|---|---|---|---|---|---|---|---|---|---|---|---|---|---|---|
| Met | Ser | Val | Met | Pro | Leu | Arg | Ser | Asp | Gly | Ser | Leu | Cys | Leu | Met | Glu |
| 1 | | | | 5 | | | | | 10 | | | | | 15 | |
| Ala | Leu | Asn | Arg | Ser | Ser | His | Ser | Asn | His | His | Gln | Asp | Ser | Ser | Pro |
| | | | 20 | | | | | 25 | | | | | 30 | | |
| Lys | Val | Glu | Asp | Phe | Phe | Gly | Thr | His | His | Asn | Asn | Thr | Ser | His | Lys |
| | | 35 | | | | | 40 | | | | | 45 | | | |
| Glu | Ala | Met | Asp | Leu | Ser | Leu | Asp | Ser | Leu | Phe | Tyr | Asn | Thr | Thr | His |
| 50 | | | | | 55 | | | | | 60 | | | | | |
| Glu | Pro | Asn | Thr | Thr | Thr | Asn | Phe | Gln | Glu | Phe | Ser | Phe | Pro | Gln | |
| 65 | | | | | 70 | | | | | 75 | | | | | 80 |
| Thr | Arg | Asn | His | Glu | Glu | Thr | Arg | Asn | Tyr | Gly | Asn | Asp | Pro | Ser | |
| | | | | 85 | | | | | 90 | | | | | 95 | |
| Leu | Thr | His | Gly | Gly | Ser | Phe | Asn | Val | Gly | Val | Tyr | Gly | Glu | Phe | Gln |
| | | | | 100 | | | | | 105 | | | | | 110 | |
| Gln | Ser | Leu | Ser | Leu | Ser | Met | Ser | Pro | Gly | Ser | Gln | Ser | Ser | Cys | Ile |
| | | | 115 | | | | | 120 | | | | | 125 | | |
| Thr | Gly | Ser | His | His | His | Gln | Gln | Asn | Gln | Asn | Gln | Asn | His | Gln | Ser |
| | 130 | | | | | 135 | | | | | 140 | | | | |
| Gln | Asn | His | Gln | Gln | Ile | Ser | Glu | Ala | Leu | Val | Glu | Thr | Ser | Val | Gly |
| 145 | | | | | 150 | | | | | 155 | | | | | 160 |
| Phe | Glu | Thr | Thr | Thr | Met | Ala | Ala | Ala | Lys | Lys | Lys | Arg | Gly | Gln | Glu |
| | | | | 165 | | | | | 170 | | | | | 175 | |
| Asp | Val | Val | Val | Gly | Gln | Lys | Gln | Ile | Val | His | Arg | Lys | Ser | Ile | |
| | | | 180 | | | | | 185 | | | | | 190 | | |
| Asp | Thr | Phe | Gly | Gln | Arg | Thr | Ser | Gln | Tyr | Arg | Gly | Val | Thr | Arg | His |
| | | | 195 | | | | | 200 | | | | | 205 | | |
| Arg | Trp | Thr | Gly | Arg | Tyr | Glu | Ala | His | Leu | Trp | Asp | Asn | Ser | Phe | Lys |
| | 210 | | | | | 215 | | | | | 220 | | | | |
| Lys | Glu | Gly | His | Ser | Arg | Lys | Gly | Arg | Gln | Val | Tyr | Leu | Gly | Gly | Tyr |
| 225 | | | | | 230 | | | | | 235 | | | | | 240 |
| Asp | Met | Glu | Glu | Lys | Ala | Ala | Arg | Ala | Tyr | Asp | Leu | Ala | Ala | Leu | Lys |
| | | | | 245 | | | | | 250 | | | | | 255 | |
| Tyr | Trp | Gly | Pro | Ser | Thr | His | Thr | Asn | Phe | Ser | Ala | Glu | Asn | Tyr | Gln |
| | | | 260 | | | | | 265 | | | | | 270 | | |
| Lys | Glu | Ile | Glu | Asp | Met | Lys | Asn | Met | Thr | Arg | Gln | Glu | Tyr | Val | Ala |
| | | | 275 | | | | | 280 | | | | | 285 | | |
| His | Leu | Arg | Arg | Lys | Ser | Ser | Gly | Phe | Ser | Arg | Gly | Ala | Ser | Ile | Tyr |
| | 290 | | | | | 295 | | | | | 300 | | | | |
| Arg | Gly | Val | Thr | Arg | His | His | Gln | His | Gly | Arg | Trp | Gln | Ala | Arg | Ile |
| 305 | | | | | 310 | | | | | 315 | | | | | 320 |
| Gly | Arg | Val | Ala | Gly | Asn | Lys | Asp | Leu | Tyr | Leu | Gly | Thr | Phe | Gly | Thr |
| | | | | 325 | | | | | 330 | | | | | 335 | |
| Gln | Glu | Glu | Ala | Ala | Glu | Ala | Tyr | Asp | Val | Ala | Ala | Ile | Lys | Phe | Arg |
| | | | 340 | | | | | 345 | | | | | 350 | | |
| Gly | Thr | Asn | Ala | Val | Thr | Asn | Phe | Asp | Ile | Thr | Arg | Tyr | Asp | Val | Asp |
| | | 355 | | | | | 360 | | | | | 365 | | | |
| Arg | Ile | Met | Ser | Ser | Asn | Thr | Leu | Leu | Ser | Gly | Glu | Leu | Ala | Arg | Arg |
| 370 | | | | | 375 | | | | | 380 | | | | | |

```
Asn Asn Asn Ser Ile Val Val Arg Asn Thr Glu Asp Gln Thr Ala Leu
385                 390                 395                 400

Asn Ala Val Val Glu Gly Gly Ser Asn Lys Glu Val Ser Thr Pro Glu
            405                 410                 415

Arg Leu Leu Ser Phe Pro Ala Ile Phe Ala Leu Pro Gln Val Asn Gln
            420                 425                 430

Lys Met Phe Gly Ser Asn Met Gly Gly Asn Met Ser Pro Trp Thr Ser
            435                 440                 445

Asn Pro Asn Ala Glu Leu Lys Thr Val Ala Leu Thr Leu Pro Gln Met
        450                 455                 460

Pro Val Phe Ala Ala Trp Ala Asp Ser
465                 470

<210> SEQ ID NO 10
<211> LENGTH: 308
<212> TYPE: PRT
<213> ORGANISM: Artificial Sequence
<220> FEATURE:
<223> OTHER INFORMATION: Description of Artificial Sequence:structurally
      altered ANT protein ANTDN2

<400> SEQUENCE: 10

Met Ala Ala Lys Lys Lys Arg Gly Gln Glu Asp Val Val Val
1               5                   10                  15

Gly Gln Lys Gln Ile Val His Arg Lys Ser Ile Asp Thr Phe Gly Gln
            20                  25                  30

Arg Thr Ser Gln Tyr Arg Gly Val Thr Arg His Arg Trp Thr Gly Arg
            35                  40                  45

Tyr Glu Ala His Leu Trp Asp Asn Ser Phe Lys Lys Glu Gly His Ser
        50                  55                  60

Arg Lys Gly Arg Gln Val Tyr Leu Gly Gly Tyr Asp Met Glu Glu Lys
65                  70                  75                  80

Ala Ala Arg Ala Tyr Asp Leu Ala Ala Leu Lys Tyr Trp Gly Pro Ser
                85                  90                  95

Thr His Thr Asn Phe Ser Ala Glu Asn Tyr Gln Lys Glu Ile Glu Asp
            100                 105                 110

Met Lys Asn Met Thr Arg Gln Glu Tyr Val Ala His Leu Arg Arg Lys
        115                 120                 125

Ser Ser Gly Phe Ser Arg Gly Ala Ser Ile Tyr Arg Gly Val Thr Arg
130                 135                 140

His His Gln His Gly Arg Trp Gln Ala Arg Ile Gly Arg Val Ala Gly
145                 150                 155                 160

Asn Lys Asp Leu Tyr Leu Gly Thr Phe Gly Thr Gln Glu Glu Ala Ala
                165                 170                 175

Glu Ala Tyr Asp Val Ala Ala Ile Lys Phe Arg Gly Thr Asn Ala Val
            180                 185                 190

Thr Asn Phe Asp Ile Thr Arg Tyr Asp Val Asp Arg Ile Met Ser Ser
        195                 200                 205

Asn Thr Leu Leu Ser Gly Glu Leu Ala Arg Arg Asn Asn Ser Ile
    210                 215                 220

Val Val Arg Asn Thr Glu Asp Gln Thr Ala Leu Asn Ala Val Val Glu
225                 230                 235                 240

Gly Gly Ser Asn Lys Glu Val Ser Thr Pro Glu Arg Leu Leu Ser Phe
                245                 250                 255

Pro Ala Ile Phe Ala Leu Pro Gln Val Asn Gln Lys Met Phe Gly Ser
```

```
                        260                 265                 270
Asn Met Gly Gly Asn Met Ser Pro Trp Thr Ser Asn Pro Asn Ala Glu
            275                 280                 285

Leu Lys Thr Val Ala Leu Thr Leu Pro Gln Met Pro Val Phe Ala Ala
    290                 295                 300

Trp Ala Asp Ser
305

<210> SEQ ID NO 11
<211> LENGTH: 277
<212> TYPE: PRT
<213> ORGANISM: Artificial Sequence
<220> FEATURE:
<223> OTHER INFORMATION: Description of Artificial Sequence:structurally
      altered ANT protein ANTDN3

<400> SEQUENCE: 11

Met Arg Thr Ser Gln Tyr Arg Gly Val Thr Arg His Arg Trp Thr Gly
  1               5                  10                  15

Arg Tyr Glu Ala His Leu Trp Asp Asn Ser Phe Lys Lys Glu Gly His
                 20                  25                  30

Ser Arg Lys Gly Arg Gln Val Tyr Leu Gly Gly Tyr Asp Met Glu Glu
            35                  40                  45

Lys Ala Ala Arg Ala Tyr Asp Leu Ala Ala Leu Lys Tyr Trp Gly Pro
     50                  55                  60

Ser Thr His Thr Asn Phe Ser Ala Glu Asn Tyr Gln Lys Glu Ile Glu
 65                  70                  75                  80

Asp Met Lys Asn Met Thr Arg Gln Glu Tyr Val Ala His Leu Arg Arg
                 85                  90                  95

Lys Ser Ser Gly Phe Ser Arg Gly Ala Ser Ile Tyr Arg Gly Val Thr
            100                 105                 110

Arg His His Gln His Gly Arg Trp Gln Ala Arg Ile Gly Arg Val Ala
        115                 120                 125

Gly Asn Lys Asp Leu Tyr Leu Gly Thr Phe Gly Thr Gln Glu Glu Ala
    130                 135                 140

Ala Glu Ala Tyr Asp Val Ala Ala Ile Lys Phe Arg Gly Thr Asn Ala
145                 150                 155                 160

Val Thr Asn Phe Asp Ile Thr Arg Tyr Asp Val Asp Arg Ile Met Ser
                165                 170                 175

Ser Asn Thr Leu Leu Ser Gly Glu Leu Ala Arg Arg Asn Asn Asn Ser
            180                 185                 190

Ile Val Val Arg Asn Thr Glu Asp Gln Thr Ala Leu Asn Ala Val Val
        195                 200                 205

Glu Gly Gly Ser Asn Lys Glu Val Ser Thr Pro Glu Arg Leu Leu Ser
    210                 215                 220

Phe Pro Ala Ile Phe Ala Leu Pro Gln Val Asn Gln Lys Met Phe Gly
225                 230                 235                 240

Ser Asn Met Gly Gly Asn Met Ser Pro Trp Thr Ser Asn Pro Asn Ala
                245                 250                 255

Glu Leu Lys Thr Val Ala Leu Thr Leu Pro Gln Met Pro Val Phe Ala
            260                 265                 270

Ala Trp Ala Asp Ser
        275

<210> SEQ ID NO 12
<211> LENGTH: 196
```

```
<212> TYPE: PRT
<213> ORGANISM: Artificial Sequence
<220> FEATURE:
<223> OTHER INFORMATION: Description of Artificial Sequence:structurally
      altered ANT protein ANTDN4

<400> SEQUENCE: 12

Met Lys Asn Met Thr Arg Gln Glu Tyr Val Ala His Leu Arg Arg Lys
 1               5                  10                  15

Ser Ser Gly Phe Ser Arg Gly Ala Ser Ile Tyr Arg Gly Val Thr Arg
            20                  25                  30

His His Gln His Gly Arg Trp Gln Ala Arg Ile Gly Arg Val Ala Gly
        35                  40                  45

Asn Lys Asp Leu Tyr Leu Gly Thr Phe Gly Thr Gln Glu Glu Ala Ala
    50                  55                  60

Glu Ala Tyr Asp Val Ala Ala Ile Lys Phe Arg Gly Thr Asn Ala Val
 65                  70                  75                  80

Thr Asn Phe Asp Ile Thr Arg Tyr Asp Val Asp Arg Ile Met Ser Ser
                85                  90                  95

Asn Thr Leu Leu Ser Gly Glu Leu Ala Arg Arg Asn Asn Ser Ile
            100                 105                 110

Val Val Arg Asn Thr Glu Asp Gln Thr Ala Leu Asn Ala Val Val Glu
        115                 120                 125

Gly Gly Ser Asn Lys Glu Val Ser Thr Pro Glu Arg Leu Leu Ser Phe
    130                 135                 140

Pro Ala Ile Phe Ala Leu Pro Gln Val Asn Gln Lys Met Phe Gly Ser
145                 150                 155                 160

Asn Met Gly Gly Asn Met Ser Pro Trp Thr Ser Asn Pro Asn Ala Glu
                165                 170                 175

Leu Lys Thr Val Ala Leu Thr Leu Pro Gln Met Pro Val Phe Ala Ala
            180                 185                 190

Trp Ala Asp Ser
        195

<210> SEQ ID NO 13
<211> LENGTH: 452
<212> TYPE: PRT
<213> ORGANISM: Artificial Sequence
<220> FEATURE:
<223> OTHER INFORMATION: Description of Artificial Sequence:structurally
      altered ANT protein ANTDC1

<400> SEQUENCE: 13

Met Lys Ser Phe Cys Asp Asn Asp Asn Asn His Ser Asn Thr Thr
 1               5                  10                  15

Asn Leu Leu Gly Phe Ser Leu Ser Ser Asn Met Met Lys Met Gly Gly
            20                  25                  30

Arg Gly Gly Arg Glu Ala Ile Tyr Ser Ser Thr Ser Ser Ala Ala
        35                  40                  45

Thr Ser Ser Ser Val Pro Pro Gln Leu Val Val Gly Asp Asn Thr
    50                  55                  60

Ser Asn Phe Gly Val Cys Tyr Gly Ser Asn Pro Asn Gly Gly Ile Tyr
 65                  70                  75                  80

Ser His Met Ser Val Met Pro Leu Arg Ser Asp Gly Ser Leu Cys Leu
                85                  90                  95

Met Glu Ala Leu Asn Arg Ser Ser His Ser Asn His His Gln Asp Ser
            100                 105                 110
```

```
Ser Pro Lys Val Glu Asp Phe Phe Gly Thr His His Asn Asn Thr Ser
    115                 120                 125

His Lys Glu Ala Met Asp Leu Ser Leu Asp Ser Leu Phe Tyr Asn Thr
    130                 135                 140

Thr His Glu Pro Asn Thr Thr Asn Phe Gln Glu Phe Phe Ser Phe
145                 150                 155                 160

Pro Gln Thr Arg Asn His Glu Glu Thr Arg Asn Tyr Gly Asn Asp
                165                 170                 175

Pro Ser Leu Thr His Gly Gly Ser Phe Asn Val Gly Val Tyr Gly Glu
                180                 185                 190

Phe Gln Gln Ser Leu Ser Leu Ser Met Ser Pro Gly Ser Gln Ser Ser
        195                 200                 205

Cys Ile Thr Gly Ser His His His Gln Gln Asn Gln Asn Gln Asn His
    210                 215                 220

Gln Ser Gln Asn His Gln Gln Ile Ser Glu Ala Leu Val Glu Thr Ser
225                 230                 235                 240

Val Gly Phe Glu Thr Thr Thr Met Ala Ala Ala Lys Lys Lys Arg Gly
                245                 250                 255

Gln Glu Asp Val Val Val Gly Gln Lys Gln Ile Val His Arg Lys
                260                 265                 270

Ser Ile Asp Thr Phe Gly Gln Arg Thr Ser Gln Tyr Arg Gly Val Thr
            275                 280                 285

Arg His Arg Trp Thr Gly Arg Tyr Glu Ala His Leu Trp Asp Asn Ser
        290                 295                 300

Phe Lys Lys Glu Gly His Ser Arg Lys Gly Arg Gln Val Tyr Leu Gly
305                 310                 315                 320

Gly Tyr Asp Met Glu Glu Lys Ala Ala Arg Ala Tyr Asp Leu Ala Ala
                325                 330                 335

Leu Lys Tyr Trp Gly Pro Ser Thr His Thr Asn Phe Ser Ala Glu Asn
                340                 345                 350

Tyr Gln Lys Glu Ile Glu Asp Met Lys Asn Met Thr Arg Gln Glu Tyr
        355                 360                 365

Val Ala His Leu Arg Arg Lys Ser Ser Gly Phe Ser Arg Gly Ala Ser
    370                 375                 380

Ile Tyr Arg Gly Val Thr Arg His His Gln His Gly Arg Trp Gln Ala
385                 390                 395                 400

Arg Ile Gly Arg Val Ala Gly Asn Lys Asp Leu Tyr Leu Gly Thr Phe
                405                 410                 415

Gly Thr Gln Glu Glu Ala Ala Glu Ala Tyr Asp Val Ala Ala Ile Lys
                420                 425                 430

Phe Arg Gly Thr Asn Ala Val Thr Asn Phe Asp Ile Thr Arg Tyr Asp
        435                 440                 445

Val Asp Arg Ile
    450

<210> SEQ ID NO 14
<211> LENGTH: 357
<212> TYPE: PRT
<213> ORGANISM: Artificial Sequence
<220> FEATURE:
<223> OTHER INFORMATION: Description of Artificial Sequence:structurally
      altered ANT protein ANTDC2

<400> SEQUENCE: 14

Met Lys Ser Phe Cys Asp Asn Asp Asp Asn Asn His Ser Asn Thr Thr
1               5                   10                  15
```

-continued

```
Asn Leu Leu Gly Phe Ser Leu Ser Ser Asn Met Met Lys Met Gly Gly
             20                  25                  30

Arg Gly Gly Arg Glu Ala Ile Tyr Ser Ser Thr Ser Ser Ala Ala
         35                  40                  45

Thr Ser Ser Ser Val Pro Pro Gln Leu Val Gly Asp Asn Thr
     50                  55                  60

Ser Asn Phe Gly Val Cys Tyr Gly Ser Asn Pro Asn Gly Gly Ile Tyr
 65                  70                  75                  80

Ser His Met Ser Val Met Pro Leu Arg Ser Asp Gly Ser Leu Cys Leu
                 85                  90                  95

Met Glu Ala Leu Asn Arg Ser Ser His Ser Asn His His Gln Asp Ser
            100                 105                 110

Ser Pro Lys Val Glu Asp Phe Phe Gly Thr His His Asn Asn Thr Ser
            115                 120                 125

His Lys Glu Ala Met Asp Leu Ser Leu Asp Ser Leu Phe Tyr Asn Thr
            130                 135                 140

Thr His Glu Pro Asn Thr Thr Thr Asn Phe Gln Glu Phe Phe Ser Phe
145                 150                 155                 160

Pro Gln Thr Arg Asn His Glu Glu Thr Arg Asn Tyr Gly Asn Asp
                165                 170                 175

Pro Ser Leu Thr His Gly Gly Ser Phe Asn Val Gly Val Tyr Gly Glu
            180                 185                 190

Phe Gln Gln Ser Leu Ser Leu Ser Met Ser Pro Gly Ser Gln Ser Ser
            195                 200                 205

Cys Ile Thr Gly Ser His His His Gln Gln Asn Gln Asn Gln Asn His
210                 215                 220

Gln Ser Gln Asn His Gln Gln Ile Ser Glu Ala Leu Val Glu Thr Ser
225                 230                 235                 240

Val Gly Phe Glu Thr Thr Thr Met Ala Ala Lys Lys Lys Arg Gly
            245                 250                 255

Gln Glu Asp Val Val Val Gly Gln Lys Gln Ile Val His Arg Lys
            260                 265                 270

Ser Ile Asp Thr Phe Gly Gln Arg Thr Ser Gln Tyr Arg Gly Val Thr
275                 280                 285

Arg His Arg Trp Thr Gly Arg Tyr Glu Ala His Leu Trp Asp Asn Ser
            290                 295                 300

Phe Lys Lys Glu Gly His Ser Arg Lys Gly Arg Gln Val Tyr Leu Gly
305                 310                 315                 320

Gly Tyr Asp Met Glu Glu Lys Ala Ala Arg Ala Tyr Asp Leu Ala Ala
                325                 330                 335

Leu Lys Tyr Trp Gly Pro Ser Thr His Thr Asn Phe Ser Ala Glu Asn
            340                 345                 350

Tyr Gln Lys Glu Ile
            355

<210> SEQ ID NO 15
<211> LENGTH: 370
<212> TYPE: PRT
<213> ORGANISM: Artificial Sequence
<220> FEATURE:
<223> OTHER INFORMATION: Description of Artificial Sequence:structurally
      altered ANT protein ANTDNC1

<400> SEQUENCE: 15

Met Ser Val Met Pro Leu Arg Ser Asp Gly Ser Leu Cys Leu Met Glu
```

-continued

```
  1               5              10              15
Ala Leu Asn Arg Ser Ser His Ser Asn His His Gln Asp Ser Ser Pro
             20                  25                  30
Lys Val Glu Asp Phe Phe Gly Thr His His Asn Asn Thr Ser His Lys
             35                  40                  45
Glu Ala Met Asp Leu Ser Leu Asp Ser Leu Phe Tyr Asn Thr Thr His
             50                  55                  60
Glu Pro Asn Thr Thr Thr Asn Phe Gln Glu Phe Ser Phe Pro Gln
 65                  70                  75                  80
Thr Arg Asn His Glu Glu Glu Thr Arg Asn Tyr Gly Asn Asp Pro Ser
                 85                  90                  95
Leu Thr His Gly Gly Ser Phe Asn Val Gly Val Tyr Gly Glu Phe Gln
                100                 105                 110
Gln Ser Leu Ser Leu Ser Met Ser Pro Gly Ser Gln Ser Ser Cys Ile
            115                 120                 125
Thr Gly Ser His His His Gln Gln Asn Gln Asn Gln Asn His Gln Ser
            130                 135                 140
Gln Asn His Gln Gln Ile Ser Glu Ala Leu Val Glu Thr Ser Val Gly
145                 150                 155                 160
Phe Glu Thr Thr Thr Met Ala Ala Ala Lys Lys Lys Arg Gly Gln Glu
                165                 170                 175
Asp Val Val Val Gly Gln Lys Gln Ile Val His Arg Lys Ser Ile
                180                 185                 190
Asp Thr Phe Gly Gln Arg Thr Ser Gln Tyr Arg Gly Val Thr Arg His
            195                 200                 205
Arg Trp Thr Gly Arg Tyr Glu Ala His Leu Trp Asp Asn Ser Phe Lys
210                 215                 220
Lys Glu Gly His Ser Arg Lys Gly Arg Gln Val Tyr Leu Gly Gly Tyr
225                 230                 235                 240
Asp Met Glu Glu Lys Ala Ala Arg Ala Tyr Asp Leu Ala Ala Leu Lys
                245                 250                 255
Tyr Trp Gly Pro Ser Thr His Thr Asn Phe Ser Ala Glu Asn Tyr Gln
                260                 265                 270
Lys Glu Ile Glu Asp Met Lys Asn Met Thr Arg Gln Glu Tyr Val Ala
            275                 280                 285
His Leu Arg Arg Lys Ser Ser Gly Phe Ser Arg Gly Ala Ser Ile Tyr
            290                 295                 300
Arg Gly Val Thr Arg His His Gln His Gly Arg Trp Gln Ala Arg Ile
305                 310                 315                 320
Gly Arg Val Ala Gly Asn Lys Asp Leu Tyr Leu Gly Thr Phe Gly Thr
                325                 330                 335
Gln Glu Glu Ala Ala Glu Ala Tyr Asp Val Ala Ala Ile Lys Phe Arg
            340                 345                 350
Gly Thr Asn Ala Val Thr Asn Phe Asp Ile Thr Arg Tyr Asp Val Asp
            355                 360                 365
Arg Ile
370
```

<210> SEQ ID NO 16
<211> LENGTH: 275
<212> TYPE: PRT
<213> ORGANISM: Artificial Sequence
<220> FEATURE:
<223> OTHER INFORMATION: Description of Artificial Sequence:structurally altered ANT protein ANTDNC2

<400> SEQUENCE: 16

```
Met Ser Val Met Pro Leu Arg Ser Asp Gly Ser Leu Cys Leu Met Glu
 1               5                  10                  15

Ala Leu Asn Arg Ser Ser His Ser Asn His His Gln Asp Ser Ser Pro
            20                  25                  30

Lys Val Glu Asp Phe Phe Gly Thr His His Asn Asn Thr Ser His Lys
         35                  40                  45

Glu Ala Met Asp Leu Ser Leu Asp Ser Leu Phe Tyr Asn Thr Thr His
     50                  55                  60

Glu Pro Asn Thr Thr Thr Asn Phe Gln Glu Phe Phe Ser Phe Pro Gln
 65                  70                  75                  80

Thr Arg Asn His Glu Glu Glu Thr Arg Asn Tyr Gly Asn Asp Pro Ser
                 85                  90                  95

Leu Thr His Gly Gly Ser Phe Asn Val Gly Val Tyr Gly Glu Phe Gln
            100                 105                 110

Gln Ser Leu Ser Leu Ser Met Ser Pro Gly Ser Gln Ser Ser Cys Ile
        115                 120                 125

Thr Gly Ser His His Gln Gln Asn Gln Asn Gln Asn His Gln Ser
    130                 135                 140

Gln Asn His Gln Gln Ile Ser Glu Ala Leu Val Glu Thr Ser Val Gly
145                 150                 155                 160

Phe Glu Thr Thr Thr Met Ala Ala Lys Lys Arg Gly Gln Glu
                165                 170                 175

Asp Val Val Val Gly Gln Lys Gln Ile Val His Arg Lys Ser Ile
            180                 185                 190

Asp Thr Phe Gly Gln Arg Thr Ser Gln Tyr Arg Gly Val Thr Arg His
        195                 200                 205

Arg Trp Thr Gly Arg Tyr Glu Ala His Leu Trp Asp Asn Ser Phe Lys
210                 215                 220

Lys Glu Gly His Ser Arg Lys Gly Arg Gln Val Tyr Leu Gly Gly Tyr
225                 230                 235                 240

Asp Met Glu Glu Lys Ala Ala Arg Ala Tyr Asp Leu Ala Ala Leu Lys
                245                 250                 255

Tyr Trp Gly Pro Ser Thr His Thr Asn Phe Ser Ala Gly Asn Tyr Gln
                260                 265                 270

Lys Glu Ile
        275
```

<210> SEQ ID NO 17
<211> LENGTH: 205
<212> TYPE: PRT
<213> ORGANISM: Artificial Sequence
<220> FEATURE:
<223> OTHER INFORMATION: Description of Artificial Sequence:structurally
      altered ANT protein ANTDNC3

<400> SEQUENCE: 17

```
Met Ala Ala Lys Lys Lys Arg Gly Gln Glu Asp Val Val Val Val
 1               5                  10                  15

Gly Gln Lys Gln Ile Val His Arg Lys Ser Ile Asp Thr Phe Gly Gln
            20                  25                  30

Arg Thr Ser Gln Tyr Arg Gly Val Thr Arg His Arg Trp Thr Gly Arg
         35                  40                  45

Tyr Glu Ala His Leu Trp Asp Asn Ser Phe Lys Lys Glu Gly His Ser
     50                  55                  60
```

Arg Lys Gly Arg Gln Val Tyr Leu Gly Gly Tyr Asp Met Glu Glu Lys
65                  70                  75                  80

Ala Ala Arg Ala Tyr Asp Leu Ala Ala Leu Lys Tyr Trp Gly Pro Ser
                85                  90                  95

Thr His Thr Asn Phe Ser Ala Glu Asn Tyr Gln Lys Glu Ile Glu Asp
            100                 105                 110

Met Lys Asn Met Thr Arg Gln Glu Tyr Val Ala His Leu Arg Arg Lys
        115                 120                 125

Ser Ser Gly Phe Ser Arg Gly Ala Ser Ile Tyr Arg Gly Val Thr Arg
    130                 135                 140

His His Gln His Gly Arg Trp Gln Ala Arg Ile Gly Arg Val Ala Gly
145                 150                 155                 160

Asn Lys Asp Leu Tyr Leu Gly Thr Phe Gly Thr Gln Glu Glu Ala Ala
                165                 170                 175

Glu Ala Tyr Asp Val Ala Ala Ile Lys Phe Arg Gly Thr Asn Ala Val
            180                 185                 190

Thr Asn Phe Asp Ile Thr Arg Tyr Asp Val Asp Arg Ile
        195                 200                 205

<210> SEQ ID NO 18
<211> LENGTH: 110
<212> TYPE: PRT
<213> ORGANISM: Artificial Sequence
<220> FEATURE:
<223> OTHER INFORMATION: Description of Artificial Sequence:structurally
      altered ANT protein ANTDNC4

<400> SEQUENCE: 18

Met Ala Ala Ala Lys Lys Lys Arg Gly Gln Glu Asp Val Val Val
1               5                   10                  15

Gly Gln Lys Gln Ile Val His Arg Lys Ser Ile Asp Thr Phe Gly Gln
                20                  25                  30

Arg Thr Ser Gln Tyr Arg Gly Val Thr Arg His Arg Trp Thr Gly Arg
            35                  40                  45

Tyr Glu Ala His Leu Trp Asp Asn Ser Phe Lys Lys Glu Gly His Ser
        50                  55                  60

Arg Lys Gly Arg Gln Val Tyr Leu Gly Gly Tyr Asp Met Glu Glu Lys
65                  70                  75                  80

Ala Ala Arg Ala Tyr Asp Leu Ala Ala Leu Lys Tyr Trp Gly Pro Ser
                85                  90                  95

Thr His Thr Asn Phe Ser Ala Glu Asn Tyr Gln Lys Glu Ile
            100                 105                 110

<210> SEQ ID NO 19
<211> LENGTH: 174
<212> TYPE: PRT
<213> ORGANISM: Artificial Sequence
<220> FEATURE:
<223> OTHER INFORMATION: Description of Artificial Sequence:structurally
      altered ANT protein ANTDNC5

<400> SEQUENCE: 19

Met Arg Thr Ser Gln Tyr Arg Gly Val Thr Arg His Arg Trp Thr Gly
1               5                   10                  15

Arg Tyr Glu Ala His Leu Trp Asp Asn Ser Phe Lys Lys Glu Gly His
                20                  25                  30

Ser Arg Lys Gly Arg Gln Val Tyr Leu Gly Gly Tyr Asp Met Glu Glu
            35                  40                  45

```
Lys Ala Ala Arg Ala Tyr Asp Leu Ala Ala Leu Lys Tyr Trp Gly Pro
 50                  55                  60

Ser Thr His Thr Asn Phe Ser Ala Glu Asn Tyr Gln Lys Glu Ile Glu
 65                  70                  75                  80

Asp Met Lys Asn Met Thr Arg Gln Glu Tyr Val Ala His Leu Arg Arg
                 85                  90                  95

Lys Ser Ser Gly Phe Ser Arg Gly Ala Ser Ile Tyr Arg Gly Val Thr
            100                 105                 110

Arg His His Gln His Gly Arg Trp Gln Ala Arg Ile Gly Arg Val Ala
        115                 120                 125

Gly Asn Lys Asp Leu Tyr Leu Gly Thr Phe Gly Thr Gln Glu Glu Ala
    130                 135                 140

Ala Glu Ala Tyr Asp Val Ala Ala Ile Lys Phe Arg Gly Thr Asn Ala
145                 150                 155                 160

Val Thr Asn Phe Asp Ile Thr Arg Tyr Asp Val Asp Arg Ile
                165                 170

<210> SEQ ID NO 20
<211> LENGTH: 78
<212> TYPE: PRT
<213> ORGANISM: Artificial Sequence
<220> FEATURE:
<223> OTHER INFORMATION: Description of Artificial Sequence:structurally
      altered ANT protein ANTDNC6

<400> SEQUENCE: 20

Arg Thr Ser Gln Tyr Arg Gly Val Thr Arg His Arg Trp Thr Gly Arg
  1               5                  10                  15

Tyr Glu Ala His Leu Trp Asp Asn Ser Phe Lys Lys Glu Gly His Ser
                 20                  25                  30

Arg Lys Gly Arg Gln Val Tyr Leu Gly Gly Tyr Asp Met Glu Glu Lys
            35                  40                  45

Ala Ala Arg Ala Tyr Asp Leu Ala Ala Leu Lys Tyr Trp Gly Pro Ser
        50                  55                  60

Thr His Thr Asn Phe Ser Ala Glu Asn Tyr Gln Lys Glu Ile
 65                  70                  75

<210> SEQ ID NO 21
<211> LENGTH: 555
<212> TYPE: PRT
<213> ORGANISM: Artificial Sequence
<220> FEATURE:
<223> OTHER INFORMATION: Description of Artificial Sequence:structurally
      altered ANT protein ANTmNLS

<400> SEQUENCE: 21

Met Lys Ser Phe Cys Asp Asn Asp Asn Asn His Ser Asn Thr Thr
  1               5                  10                  15

Asn Leu Leu Gly Phe Ser Leu Ser Ser Asn Met Met Lys Met Gly Gly
                 20                  25                  30

Arg Gly Gly Arg Glu Ala Ile Tyr Ser Ser Thr Ser Ser Ala Ala
            35                  40                  45

Thr Ser Ser Ser Ser Val Pro Pro Gln Leu Val Val Gly Asp Asn Thr
         50                  55                  60

Ser Asn Phe Gly Val Cys Tyr Gly Ser Asn Pro Asn Gly Gly Ile Tyr
 65                  70                  75                  80

Ser His Met Ser Val Met Pro Leu Arg Ser Asp Gly Ser Leu Cys Leu
                 85                  90                  95
```

```
Met Glu Ala Leu Asn Arg Ser Ser His Ser Asn His His Gln Asp Ser
            100                 105                 110

Ser Pro Lys Val Glu Asp Phe Phe Gly Thr His His Asn Asn Thr Ser
        115                 120                 125

His Lys Glu Ala Met Asp Leu Ser Leu Asp Ser Leu Phe Tyr Asn Thr
    130                 135                 140

Thr His Glu Pro Asn Thr Thr Asn Phe Gln Glu Phe Phe Ser Phe
145                 150                 155                 160

Pro Gln Thr Arg Asn His Glu Glu Thr Arg Asn Tyr Gly Asn Asp
                165                 170                 175

Pro Ser Leu Thr His Gly Gly Ser Phe Asn Val Gly Val Tyr Gly Glu
            180                 185                 190

Phe Gln Gln Ser Leu Ser Leu Ser Met Ser Pro Gly Ser Gln Ser Ser
        195                 200                 205

Cys Ile Thr Gly Ser His His His Gln Gln Asn Gln Asn Gln Asn His
    210                 215                 220

Gln Ser Gln Asn His Gln Gln Ile Ser Glu Ala Leu Val Glu Thr Ser
225                 230                 235                 240

Val Gly Phe Glu Thr Thr Thr Met Ala Ala Ala Ser Ser Thr Arg Gly
                245                 250                 255

Gln Glu Asp Val Val Val Gly Gln Lys Gln Ile Val His Arg Lys
            260                 265                 270

Ser Ile Asp Thr Phe Gly Gln Arg Thr Ser Gln Tyr Arg Gly Val Thr
        275                 280                 285

Arg His Arg Trp Thr Gly Arg Tyr Glu Ala His Leu Trp Asp Asn Ser
    290                 295                 300

Phe Lys Lys Glu Gly His Ser Arg Lys Gly Arg Gln Val Tyr Leu Gly
305                 310                 315                 320

Gly Tyr Asp Met Glu Glu Lys Ala Ala Arg Ala Tyr Asp Leu Ala Ala
                325                 330                 335

Leu Lys Tyr Trp Gly Pro Ser Thr His Thr Asn Phe Ser Ala Glu Asn
            340                 345                 350

Tyr Gln Lys Glu Ile Glu Asp Met Lys Asn Met Thr Arg Gln Glu Tyr
        355                 360                 365

Val Ala His Leu Arg Arg Lys Ser Ser Gly Phe Ser Arg Gly Ala Ser
    370                 375                 380

Ile Tyr Arg Gly Val Thr Arg His His Gln His Gly Arg Trp Gln Ala
385                 390                 395                 400

Arg Ile Gly Arg Val Ala Gly Asn Lys Asp Leu Tyr Leu Gly Thr Phe
                405                 410                 415

Gly Thr Gln Glu Glu Ala Ala Glu Ala Tyr Asp Val Ala Ala Ile Lys
            420                 425                 430

Phe Arg Gly Thr Asn Ala Val Thr Asn Phe Asp Ile Thr Arg Tyr Asp
        435                 440                 445

Val Asp Arg Ile Met Ser Ser Asn Thr Leu Leu Ser Gly Glu Leu Ala
    450                 455                 460

Arg Arg Asn Asn Asn Ser Ile Val Val Arg Asn Thr Glu Asp Gln Thr
465                 470                 475                 480

Ala Leu Asn Ala Val Val Glu Gly Gly Ser Asn Lys Glu Val Ser Thr
                485                 490                 495

Pro Glu Arg Leu Leu Ser Phe Pro Ala Ile Phe Ala Leu Pro Gln Val
            500                 505                 510
```

```
Asn Gln Lys Met Phe Gly Ser Asn Met Gly Gly Asn Met Ser Pro Trp
        515                 520                 525
Thr Ser Asn Pro Asn Ala Glu Leu Lys Thr Val Ala Leu Thr Leu Pro
        530                 535                 540
Gln Met Pro Val Phe Ala Ala Trp Ala Asp Ser
545                 550                 555

<210> SEQ ID NO 22
<211> LENGTH: 555
<212> TYPE: PRT
<213> ORGANISM: Artificial Sequence
<220> FEATURE:
<223> OTHER INFORMATION: Description of Artificial Sequence:structurally
      altered ANT protein ANTmRII, temperature sensitive
      mutant

<400> SEQUENCE: 22

Met Lys Ser Phe Cys Asp Asn Asp Asn Asn His Ser Asn Thr Thr
1               5                   10                  15

Asn Leu Leu Gly Phe Ser Leu Ser Ser Asn Met Met Lys Met Gly Gly
            20                  25                  30

Arg Gly Gly Arg Glu Ala Ile Tyr Ser Ser Ser Thr Ser Ser Ala Ala
        35                  40                  45

Thr Ser Ser Ser Val Pro Pro Gln Leu Val Val Gly Asp Asn Thr
    50                  55                  60

Ser Asn Phe Gly Val Cys Tyr Gly Ser Asn Pro Asn Gly Gly Ile Tyr
65              70                  75                  80

Ser His Met Ser Val Met Pro Leu Arg Ser Asp Gly Ser Leu Cys Leu
            85                  90                  95

Met Glu Ala Leu Asn Arg Ser Ser His Ser Asn His His Gln Asp Ser
            100                 105                 110

Ser Pro Lys Val Glu Asp Phe Phe Gly Thr His His Asn Asn Thr Ser
        115                 120                 125

His Lys Glu Ala Met Asp Leu Ser Leu Asp Ser Leu Phe Tyr Asn Thr
    130                 135                 140

Thr His Glu Pro Asn Thr Thr Thr Asn Phe Gln Glu Phe Phe Ser Phe
145                 150                 155                 160

Pro Gln Thr Arg Asn His Glu Glu Thr Arg Asn Tyr Gly Asn Asp
            165                 170                 175

Pro Ser Leu Thr His Gly Gly Ser Phe Asn Val Gly Val Tyr Gly Glu
        180                 185                 190

Phe Gln Gln Ser Leu Ser Leu Ser Met Ser Pro Gly Ser Gln Ser Ser
    195                 200                 205

Cys Ile Thr Gly Ser His His Gln Gln Asn Gln Asn Gln Asn His
210                 215                 220

Gln Ser Gln Asn His Gln Gln Ile Ser Glu Ala Leu Val Glu Thr Ser
225                 230                 235                 240

Val Gly Phe Glu Thr Thr Thr Met Ala Ala Ala Ser Ser Thr Arg Gly
            245                 250                 255

Gln Glu Asp Val Val Val Gly Gln Lys Gln Ile Val His Arg Lys
        260                 265                 270

Ser Ile Asp Thr Phe Gly Gln Arg Thr Ser Gln Tyr Arg Gly Val Thr
    275                 280                 285

Arg His Arg Trp Thr Gly Arg Tyr Glu Ala His Leu Trp Asp Asn Ser
290                 295                 300

Phe Lys Lys Glu Gly His Ser Arg Lys Gly Arg Gln Val Tyr Leu Gly
```

-continued

```
                305                 310                 315                 320
        Gly Tyr Asp Met Glu Glu Lys Ala Ala Arg Ala Tyr Asp Leu Ala Ala
                        325                 330                 335
        Leu Lys Tyr Trp Gly Pro Ser Thr His Thr Asn Phe Ser Ala Glu Asn
                        340                 345                 350
        Tyr Gln Lys Glu Ile Glu Asp Met Lys Asn Met Thr Arg Gln Glu Tyr
                        355                 360                 365
        Val Ala His Leu Arg Arg Lys Ser Ser Gly Phe Ser Arg Gly Ala Ser
                        370                 375                 380
        Ile Tyr Arg Gly Val Thr Arg His His Gln His Gly Arg Trp Gln Ala
        385                 390                 395                 400
        Arg Ile Gly Arg Val Ala Gly Asn Lys Asp Leu Tyr Leu Ser Thr Phe
                        405                 410                 415
        Gly Thr Gln Glu Glu Ala Ala Glu Ala Tyr Asp Val Ala Ala Ile Lys
                        420                 425                 430
        Phe Arg Gly Thr Asn Ala Val Thr Asn Phe Asp Ile Thr Arg Tyr Asp
                        435                 440                 445
        Val Asp Arg Ile Met Ser Ser Asn Thr Leu Leu Ser Gly Glu Leu Ala
        450                 455                 460
        Arg Arg Asn Asn Ser Ile Val Val Arg Asn Thr Glu Asp Gln Thr
        465                 470                 475                 480
        Ala Leu Asn Ala Val Val Glu Gly Gly Ser Asn Lys Glu Val Ser Thr
                        485                 490                 495
        Pro Glu Arg Leu Leu Ser Phe Pro Ala Ile Phe Ala Leu Pro Gln Val
                        500                 505                 510
        Asn Gln Lys Met Phe Gly Ser Asn Met Gly Gly Asn Met Ser Pro Trp
                        515                 520                 525
        Thr Ser Asn Pro Asn Ala Glu Leu Lys Thr Val Ala Leu Thr Leu Pro
                        530                 535                 540
        Gln Met Pro Val Phe Ala Ala Trp Ala Asp Ser
        545                 550                 555

<210> SEQ ID NO 23
<211> LENGTH: 314
<212> TYPE: PRT
<213> ORGANISM: Artificial Sequence
<220> FEATURE:
<223> OTHER INFORMATION: Description of Artificial Sequence:novel
      chimeric ANT protein ANT-AP2sw1

<400> SEQUENCE: 23

Met Gln Tyr Arg Gly Val Thr Arg His Arg Trp Thr Gly Arg Tyr Glu
  1               5                  10                  15
Ala His Leu Trp Asp Asn Ser Phe Lys Lys Glu Gly His Ser Arg Lys
                 20                  25                  30
Gly Arg Gln Val Tyr Leu Gly Gly Tyr Asp Met Glu Glu Lys Ala Ala
             35                  40                  45
Arg Ala Tyr Asp Leu Ala Ala Leu Lys Tyr Trp Gly Pro Ser Thr His
         50                  55                  60
Thr Asn Phe Ser Ala Glu Asn Tyr Gln Lys Glu Ile Glu Asp Met Lys
 65                  70                  75                  80
Asn Met Thr Arg Gln Glu Tyr Val Ala His Leu Arg Arg Lys Ser Ser
                 85                  90                  95
Gly Phe Ser Arg Gly Ala Ser Ile Tyr Arg Gly Val Thr Arg His His
                100                 105                 110
```

```
Gln His Gly Arg Trp Gln Ala Arg Ile Gly Arg Val Ala Gly Asn Lys
        115                 120                 125

Asp Leu Tyr Leu Ser Thr Phe Gly Thr Gln Glu Ala Ala Glu Ala
130                 135                 140

Tyr Asp Val Ala Ala Ile Lys Phe Arg Gly Thr Asn Ala Val Thr Asn
145                 150                 155                 160

Phe Asp Ile Thr Arg Tyr Asp Val Asp Arg Ile Met Ser Ser Val Gly
                165                 170                 175

Asn Pro Thr Thr Pro Gln Asp His Asn Leu Asp Leu Ser Leu Gly Asn
                180                 185                 190

Ser Ala Asn Ser Lys His Lys Ser Gln Asp Met Arg Leu Arg Met Asn
                195                 200                 205

Gln Gln Gln Gln Asp Ser Leu His Ser Asn Glu Val Leu Gly Leu Gly
            210                 215                 220

Gln Thr Gly Met Leu Asn His Thr Pro Asn Ser Asn His Gln Phe Pro
225                 230                 235                 240

Gly Ser Ser Asn Ile Gly Ser Gly Gly Phe Ser Leu Phe Pro Ala
                245                 250                 255

Ala Glu Asn His Arg Phe Asp Gly Arg Ala Ser Thr Asn Gln Val Leu
                260                 265                 270

Thr Asn Ala Ala Ala Ser Ser Gly Phe Ser Pro His His His Asn Gln
            275                 280                 285

Ile Phe Asn Ser Thr Ser Thr Pro His Gln Asn Trp Leu Gln Thr Asn
290                 295                 300

Gly Phe Gln Pro Pro Leu Met Arg Pro Ser
305                 310

<210> SEQ ID NO 24
<211> LENGTH: 264
<212> TYPE: PRT
<213> ORGANISM: Artificial Sequence
<220> FEATURE:
<223> OTHER INFORMATION: Description of Artificial Sequence:novel
      chimeric ANT protein ANT-AP2sw2

<400> SEQUENCE: 24

Met Ser Gln Tyr Arg Gly Val Thr Phe Tyr Arg Arg Thr Gly Arg Trp
1               5                   10                  15

Glu Ser His Ile Trp Asp Cys Gly Lys Gln Val Tyr Leu Gly Gly Phe
                20                  25                  30

Asp Thr Ala His Ala Ala Ala Arg Ala Tyr Asp Arg Ala Ala Ile Lys
            35                  40                  45

Phe Arg Gly Val Glu Ala Asp Ile Asn Phe Asn Ile Asp Asp Tyr Asp
        50                  55                  60

Asp Asp Leu Lys Gln Met Thr Asn Leu Thr Lys Glu Glu Phe Val His
65                  70                  75                  80

Val Leu Arg Arg Gln Ser Thr Gly Phe Pro Arg Gly Ser Ser Lys Tyr
                85                  90                  95

Arg Gly Val Thr Leu His Lys Cys Gly Arg Trp Glu Ala Arg Met Gly
                100                 105                 110

Gln Phe Leu Gly Lys Lys Tyr Val Tyr Leu Gly Leu Phe Asp Thr Glu
            115                 120                 125

Val Glu Ala Ala Arg Ala Tyr Asp Lys Ala Ala Ile Lys Cys Asn Gly
            130                 135                 140

Lys Asp Ala Val Thr Asn Phe Asp Pro Ser Ile Tyr Asp Glu Glu Leu
145                 150                 155                 160
```

-continued

```
Asn Ala Glu Tyr Asn Thr Leu Leu Ser Gly Glu Leu Ala Arg Arg Asn
            165                 170                 175

Asn Asn Ser Ile Val Val Arg Asn Thr Glu Asp Gln Thr Ala Leu Asn
            180                 185                 190

Ala Val Val Glu Gly Gly Ser Asn Lys Glu Val Ser Thr Pro Glu Arg
            195                 200                 205

Leu Leu Ser Phe Pro Ala Ile Phe Ala Leu Pro Gln Val Asn Gln Lys
            210                 215                 220

Met Phe Gly Ser Asn Met Gly Gly Asn Met Ser Pro Trp Thr Ser Asn
225                 230                 235                 240

Pro Asn Ala Glu Leu Lys Thr Val Ala Leu Thr Leu Pro Gln Met Pro
            245                 250                 255

Val Phe Ala Ala Trp Ala Asp Ser
            260
```

<210> SEQ ID NO 25
<211> LENGTH: 275
<212> TYPE: PRT
<213> ORGANISM: Artificial Sequence
<220> FEATURE:
<223> OTHER INFORMATION: Description of Artificial Sequence:novel
      chimeric ANT protein ANTdf1

<400> SEQUENCE: 25

```
Met Ser Gln Tyr Arg Gly Val Thr Arg His Arg Trp Thr Gly Arg Tyr
  1                 5                  10                  15

Glu Ala His Leu Trp Asp Asn Ser Phe Lys Lys Glu Gly His Ser Arg
             20                  25                  30

Lys Gly Arg Gln Val Tyr Leu Gly Gly Tyr Asp Met Glu Glu Lys Ala
             35                  40                  45

Ala Arg Ala Tyr Asp Leu Ala Ala Leu Lys Tyr Trp Gly Pro Ser Thr
             50                  55                  60

His Thr Asn Phe Ser Ala Glu Asn Tyr Gln Lys Glu Ile Glu Asp Met
 65                  70                  75                  80

Lys Asn Met Thr Arg Gln Glu Tyr Val Ala His Leu Arg Arg Lys Ser
             85                  90                  95

Ser Gly Phe Ser Arg Gly Ala Ser Ile Tyr Arg Gly Val Thr Arg His
            100                 105                 110

His Gln His Gly Arg Trp Gln Ala Arg Ile Gly Arg Val Ala Gly Asn
            115                 120                 125

Lys Asp Leu Tyr Leu Ser Thr Phe Gly Thr Gln Glu Glu Ala Ala Glu
            130                 135                 140

Ala Tyr Asp Val Ala Ala Ile Lys Phe Arg Gly Thr Asn Ala Val Thr
145                 150                 155                 160

Asn Phe Asp Ile Thr Arg Tyr Asp Val Asp Arg Ile Met Ser Ser Asn
            165                 170                 175

Thr Leu Leu Ser Gly Glu Leu Ala Arg Arg Asn Asn Asn Ser Ile Val
            180                 185                 190

Val Arg Asn Thr Glu Asp Gln Thr Ala Leu Asn Ala Val Val Glu Gly
            195                 200                 205

Gly Ser Asn Lys Glu Val Ser Thr Pro Glu Arg Leu Leu Ser Phe Pro
            210                 215                 220

Ala Ile Phe Ala Leu Pro Gln Val Asn Gln Lys Met Phe Gly Ser Asn
225                 230                 235                 240

Met Gly Gly Asn Met Ser Pro Trp Thr Ser Asn Pro Asn Ala Glu Leu
```

```
                245                 250                 255
Lys Thr Val Ala Leu Thr Leu Pro Gln Met Pro Val Phe Ala Ala Trp
            260                 265                 270

Ala Asp Ser
        275

<210> SEQ ID NO 26
<211> LENGTH: 1422
<212> TYPE: DNA
<213> ORGANISM: Artificial Sequence
<220> FEATURE:
<223> OTHER INFORMATION: Description of Artificial Sequence:truncated or
      mutated ANT cDNA transgene ANTDN1

<400> SEQUENCE: 26
atgtctgtga tgccactcag atctgatggt tctctttgct taatggaagc tctcaacaga      60
tcttctcact cgaatcacca tcaagattca tctccaaagg tggaggattt ctttgggacc    120
catcacaaca acacaagtca caagaagcc atggatctta gcttagatag tttattctac    180
aacaccactc atgagcccaa cacgactaca aactttcaag agttctttag cttccctcaa    240
accagaaacc atgaggaaga aactagaaat tacgggaatg accctagttt gacacatgga    300
gggtctttta tgtagggggt atatggggaa tttcaacagt cactgagctt atccatgagc    360
cctgggtcac aatctagctg catcactggc tctcaccacc accaacaaaa ccaaaaccaa    420
aaccaccaaa gccaaaacca ccagcagatc tctgaagctc ttgtggagac aagcgttggg    480
tttgagacga cgacaatggc ggctgcgaag aagaagaggg gacaagagga tgttgtagtt    540
gttggtcaga aacagattgt tcatagaaaa tctatcgata cttttggaca acgaacttct    600
caataccgag gcgttacaag acatagatgg actggtagat atgaagctca tctatgggac    660
aatagtttca agaaggaagg tcacagtaga aaggaagac agtttatctg ggaggttat    720 gatatggagg agaaagctgc tcgagcatat gatcttgctg cactcaagta ctgggggtccc    780 tctactcaca ccaatttctc tgcggagaat tatcagaaag agattgaaga catgaagaac    840
atgactagac aagaatatgt tgcacattg agaaggaaga gcagtggttt ctctagggggt    900 gcttccatct atagaggagt cacaagacat caccagcatg gaaggtggca agcacggatt    960
ggtagagtcg ctgaaaacaa agatctctac cttggaactt ttggaaccca agaagaagct   1020
gcagaagctt acgatgtagc agcaattaag ttccgtggca caaatgctgt gactaacttt   1080
gatatcacga ggtacgatgt tgatcgtatc atgtctagta acacactctt gtctggagag   1140
ttagcgcgaa ggaacaacaa cagcattgtc gtcaggaata ctgaagacca aaccgctcta   1200
aatgctgttg tggaaggtgg ttccaacaaa gaagtcagta ctcccgagag actcttgagt   1260
tttccggcga ttttcgcgtt gcctcaagtt aatcaaaaga tgttcggatc aaatatgggc   1320
ggaaatatga gtccttggac atcaaaccct aatgctgagc ttaagaccgt cgctcttact   1380
ttgcctcaga tgccggtttt cgctgcttgg gctgattctt ga                      1422

<210> SEQ ID NO 27
<211> LENGTH: 927
<212> TYPE: DNA
<213> ORGANISM: Artificial Sequence
<220> FEATURE:
<223> OTHER INFORMATION: Description of Artificial Sequence:truncated or
      mutated ANT cDNA transgene ANTDN2

<400> SEQUENCE: 27
atggcggctg cgaagaagaa gaggggacaa gaggatgttg tagttgttgg tcagaaacag      60
```

-continued

```
attgttcata gaaaatctat cgatactttt ggacaacgaa cttctcaata ccgaggcgtt      120
acaagacata gatggactgg tagatatgaa gctcatctat gggacaatag tttcaagaag      180
gaaggtcaca gtagaaaagg aagacaagtt tatctgggag gttatgatat ggaggagaaa      240
gctgctcgag catatgatct tgctgcactc aagtactggg gtccctctac tcacaccaat      300
ttctctgcgg agaattatca gaaagagatt gaagacatga agaacatgac tagacaagaa      360
tatgttgcac atttgagaag gaagagcagt ggtttctcta ggggtgcttc catctataga      420
ggagtcacaa gacatcacca gcatggaagg tggcaagcac ggattggtag agtcgctgga      480
aacaaagatc tctaccttgg aactttggga acccaagaag aagctgcaga gcttacgat       540 gtagcagcaa ttaagttccg tggcacaaat gctgtgacta actttgatat cacgaggtac      600
gatgttgatc gtatcatgtc tagtaacaca ctcttgtctg gagagttagc gcgaaggaac      660
aacaacagca ttgtcgtcag gaatactgaa gaccaaaccg ctctaaatgc tgttgtggaa      720
ggtggttcca caaagaagt cagtactccc gagagactct tgagttttcc ggcgattttc       780
gcgttgcctc aagttaatca aaagatgttc ggatcaaata tgggcggaaa tatgagtcct      840
tggacatcaa accctaatgc tgagcttaag accgtcgctc ttactttgcc tcagatgccg      900
gttttcgctg cttgggctga ttcttga                                         927
```

<210> SEQ ID NO 28
<211> LENGTH: 834
<212> TYPE: DNA
<213> ORGANISM: Artificial Sequence
<220> FEATURE:
<223> OTHER INFORMATION: Description of Artificial Sequence:truncated or mutated ANT cDNA transgene ANTDN3

<400> SEQUENCE: 28

```
atgcgaactt ctcaataccg aggcgttaca agacatagat ggactggtag atatgaagct       60
catctatggg acaatagttt caagaaggaa ggtcacagta gaaaaggaag acaagtttat     120 ctggaggtt atgatatgga ggagaaagct gctcgagcat atgatcttgc tgcactcaag      180 tactgggtc cctctactca caccaatttc tctgcggaga attatcagaa agagattgaa      240
gacatgaaga acatgactag acaagaatat gttgcacatt tgagaaggaa gagcagtggt      300
ttctctaggg gtgcttccat ctatagagga gtcacaagac atcaccagca tggaaggtgg      360
caagcacgga ttggtagagt cgctggaaac aaagatctct accttggaac ttttggaacc      420
caagaagaag ctgcagaagc ttacgatgta gcagcaatta agttccgtgg cacaaatgct      480
gtgactaact tgatatcac gaggtacgat gttgatcgta tcatgtctag taacacactc       540
ttgtctggag agttagcgcg aaggaacaac aacagcattg tcgtcaggaa tactgaagac      600
caaaccgctc taaatgctgt tgtggaaggt ggttccaaca agaagtcag tactcccgag       660 agactcttga gttttccggc gattttcgcg ttgcctcaag ttaatcaaaa gatgttcgga      720
tcaaatatgg gcggaaatat gagtccttgg acatcaaacc ctaatgctga gcttaagacc      780
gtcgctctta ctttgcctca gatgccggtt tcgctgctt gggctgattc ttga             834
```

<210> SEQ ID NO 29
<211> LENGTH: 591
<212> TYPE: DNA
<213> ORGANISM: Artificial Sequence
<220> FEATURE:
<223> OTHER INFORMATION: Description of Artificial Sequence:truncated or mutated ANT cDNA transgene ANTDN4

-continued

```
<400> SEQUENCE: 29
atgaagaaca tgactagaca agaatatgtt gcacatttga aaggaagag cagtggtttc      60 tctaggggtg cttccatcta tagaggagtc acaagacatc accagcatgg aaggtggcaa    120
gcacggattg gtagagtcgc tggaaacaaa gatctctacc ttggaacttt tggaacccaa    180
gaagaagctg cagaagctta cgatgtagca gcaattaagt tccgtggcac aaatgctgtg    240
actaactttg tatcacgag gtacgatgtt gatcgtatca tgtctagtaa cacactcttg    300
tctggagagt tagcgcgaag gaacaacaac agcattgtcg tcaggaatac tgaagaccaa    360
accgctctaa atgctgttgt ggaaggtggt tccaacaaag aagtcagtac tcccgagaga    420
ctcttgagtt ttccggcgat tttcgcgttg cctcaagtta atcaaaagat gttcggatca    480
aatatgggcg gaaatatgag tccttggaca tcaaacccta atgctgagct taagaccgtc    540
gctcttactt tgcctcagat gccggttttc gctgcttggg ctgattcttg a              591

<210> SEQ ID NO 30
<211> LENGTH: 1359
<212> TYPE: DNA
<213> ORGANISM: Artificial Sequence
<220> FEATURE:
<223> OTHER INFORMATION: Description of Artificial Sequence:truncated or
      mutated ANT cDNA transgene ANTDC1

<400> SEQUENCE: 30
atgaagtctt tttgtgataa tgatgataat aatcatagca acacgactaa tttgttaggg      60
ttctcattgt cttcaaatat gatgaaaatg ggaggtagag gaggtagaga agctatttac    120
tcatcttcaa cttcttcagc tgcaacttct tcttcttctg ttccacctca acttgttgtt    180
ggtgacaaca ctagcaactt tggtgtttgc tatggatcta acccaaatgg aggaatctat    240
tctcacatgt ctgtgatgcc actcagatct gatggttctc tttgcttaat ggaagctctc    300
aacagatctt ctcactcgaa tcaccatcaa gattcatctc caaaggtgga ggatttcttt    360
gggacccatc acaacaacac aagtcacaaa gaagccatgg atcttagctt agatagttta    420
ttctacaaca ccactcatga gcccaacacg actacaaact tcaagagtt ctttagcttc    480 cctcaaaacca gaaaccatga ggaagaaact agaaattacg ggaatgaccc tagtttgaca    540
catggagggt ctttttaatgt aggggtatat ggggaatttc aacagtcact gagcttatcc    600
atgagccctg ggtcacaatc tagctgcatc actggctctc accaccacca acaaaaccaa    660
aaccaaaacc accaaagcca aaccaccag cagatctctg aagctcttgt ggagacaagc    720
gttgggtttg agacgacgac aatggcggct gcgaagaaga agagggaca agaggatgtt    780 gtagttgttg gtcagaaaca gattgttcat agaaaatcta tcgatacttt tggacaacga    840
acttctcaat accgaggcgt tacaagacat agatggactg gtagatatga agctcatcta    900
tgggacaata gtttcaagaa ggaaggtcac agtagaaaag gaagcaagt ttatctggga    960 ggttatgata tggaggagaa agctgctcga gcatatgatc ttgctgcact caagtactgg    1020
ggtccctcta ctcacaccaa tttctctgcg gagaattatc agaaagagat tgaagacatg    1080
aagaacatga ctagacaaga atatgttgca catttgagaa ggaagagcag tggtttctct    1140 agggggtgctt ccatctatag aggagtcaca agacatcacc agcatggaag gtggcaagca    1200
cggattggta gagtcgctgg aaacaaagat ctctaccttg aacttttgg aacccaagaa    1260 gaagctgcag aagcttacga tgtagcagca attaagttcc gtggcacaaa tgctgtgact    1320
aactttgata tcacgaggta cgatgttgat cgtatctga                            1359
```

<210> SEQ ID NO 31
<211> LENGTH: 1074
<212> TYPE: DNA
<213> ORGANISM: Artificial Sequence
<220> FEATURE:
<223> OTHER INFORMATION: Description of Artificial Sequence:truncated or mutated ANT cDNA transgene ANTDC2

<400> SEQUENCE: 31

| | | | | | |
|---|---|---|---|---|---|
| atgaagtctt | tttgtgataa | tgatgataat | aatcatagca | acacgactaa | tttgttaggg | 60 |
| ttctcattgt | cttcaaatat | gatgaaaatg | ggaggtagag | gagtagaga | agctatttac | 120 |
| tcatcttcaa | cttcttcagc | tgcaacttct | tcttcttctg | ttccacctca | acttgttgtt | 180 |
| ggtgacaaca | ctagcaactt | tggtgtttgc | tatggatcta | acccaaatgg | aggaatctat | 240 |
| tctcacatgt | ctgtgatgcc | actcagatct | gatggttctc | tttgcttaat | ggaagctctc | 300 |
| aacagatctt | ctcactcgaa | tcaccatcaa | gattcatctc | caaaggtgga | ggatttcttt | 360 |
| gggacccatc | acaacaacac | aagtcacaaa | gaagccatgg | atcttagctt | agatagttta | 420 |
| ttctacaaca | ccactcatga | gcccaacacg | actacaaact | ttcaagagtt | ctttagcttc | 480 |
| cctcaaacca | gaaaccatga | ggaagaaact | agaaattacg | ggaatgaccc | tagtttgaca | 540 |
| catggagggt | cttttaatgt | agggtatat | ggggaatttc | aacagtcact | gagcttatcc | 600 |
| atgagccctg | gtcacaatc | tagctgcatc | actggctctc | accaccacca | acaaaaccaa | 660 |
| aaccaaaacc | accaaagcca | aaaccaccag | cagatctctg | aagctcttgt | ggagacaagc | 720 |
| gttgggtttg | agacgacgac | aatggcggct | gcgaagaaga | gaggggaca | agaggatgtt | 780 |
| gtagttgttg | gtcagaaaca | gattgttcat | agaaaatcta | tcgatacttt | tggacaacga | 840 |
| acttctcaat | accgaggcgt | tacaagacat | agatggactg | tagatatga | agctcatcta | 900 |
| tgggacaata | gtttcaagaa | ggaaggtcac | agtagaaaag | gaagacaagt | ttatctggga | 960 |
| ggttatgata | tggaggagaa | agctgctcga | gcatatgatc | ttgctgcact | caagtactgg | 1020 |
| ggtccctcta | ctcacaccaa | tttctctgcg | gagaattatc | agaaagagat | ttga | 1074 |

<210> SEQ ID NO 32
<211> LENGTH: 1113
<212> TYPE: DNA
<213> ORGANISM: Artificial Sequence
<220> FEATURE:
<223> OTHER INFORMATION: Description of Artificial Sequence:truncated or mutated ANT cDNA transgene ANTDNC1

<400> SEQUENCE: 32

| | | | | | |
|---|---|---|---|---|---|
| atgtctgtga | tgccactcag | atctgatggt | tctctttgct | taatggaagc | tctcaacaga | 60 |
| tcttctcact | cgaatcacca | tcaagattca | tctccaaagg | tggaggattt | ctttgggacc | 120 |
| catcacaaca | acacaagtca | caaagaagcc | atggatctta | gcttagatag | tttattctac | 180 |
| aacaccactc | atgagcccaa | cacgactaca | aactttcaag | agttctttag | cttccctcaa | 240 |
| accagaaacc | atgaggaaga | aactagaaat | tacgggaatg | accctagttt | gacacatgga | 300 |
| gggtctttta | atgtaggggt | atatgggaa | tttcaacagt | cactgagctt | atccatgagc | 360 |
| cctggtcac | aatctagctg | catcactggc | tctcaccacc | accaacaaaa | ccaaaaccaa | 420 |
| aaccaccaaa | gccaaaacca | ccagcagatc | tctgaagctc | ttgtggagac | aagcgttggg | 480 |
| tttgagacga | cgacaatggc | ggctgcgaag | aagaagggg | acaagagga | tgttgtagtt | 540 |
| gttggtcaga | aacagattgt | tcatagaaaa | tctatcgata | cttttggaca | acgaacttct | 600 |
| caataccgag | gcgttacaag | acatagatgg | actggtagat | atgaagctca | tctatgggac | 660 |

```
aatagtttca agaaggaagg tcacagtaga aaaggaagac aagtttatct gggaggttat      720
gatatggagg agaaagctgc tcgagcatat gatcttgctg cactcaagta ctggggtccc      780
tctactcaca ccaatttctc tgcggagaat tatcagaaag agattgaaga catgaagaac      840
atgactagac aagaatatgt tgcacatttg agaaggaaga gcagtggttt ctctaggggt      900
gcttccatct atagaggagt cacaagacat caccagcatg gaaggtggca agcacggatt      960
ggtagagtcg ctggaaacaa agatctctac cttggaactt ttggaaccca agaagaagct     1020
gcagaagctt acgatgtagc agcaattaag ttccgtggca caaatgctgt gactaacttt     1080
gatatcacga ggtacgatgt tgatcgtatc tga                                  1113

<210> SEQ ID NO 33
<211> LENGTH: 828
<212> TYPE: DNA
<213> ORGANISM: Artificial Sequence
<220> FEATURE:
<223> OTHER INFORMATION: Description of Artificial Sequence:truncated or
      mutated ANT cDNA transgene ANTDNC2

<400> SEQUENCE: 33
atgtctgtga tgccactcag atctgatggt tctctttgct taatggaagc tctcaacaga       60
tcttctcact cgaatcacca tcaagattca tctccaaagg tggaggattt ctttgggacc      120
catcacaaca acacaagtca caaagaagcc atggatctta gcttagatag tttattctac      180
aacaccactc atgagcccaa cacgactaca aactttcaag agttctttag cttccctcaa      240
accagaaacc atgaggaaga aactagaaat tacgggaatg accctagttt gacacatgga      300
gggtctttta atgtaggggt atatggggaa tttcaacagt cactgagctt atccatgagc      360
cctgggtcac aatctagctg catcactggc tctcaccacc aaacaaaaa ccaaaaccaa      420 aaccaccaaa gccaaaacca ccagcagatc tctgaagctc ttgtggagac aagcgttggg      480
tttgagacga cgacaatggc ggctgcgaag aagaagaggg acaagagga tgttgtagtt      540 gttggtcaga aacagattgt tcatagaaaa tctatcgata cttttggaca acgaacttct      600
caataccgag gcgttacaag acatagatgg actggtagat atgaagctca tctatgggac      660
aatagtttca agaaggaagg tcacagtaga aaaggaagac aagtttatct gggaggttat      720
gatatggagg agaaagctgc tcgagcatat gatcttgctg cactcaagta ctggggtccc      780
tctactcaca ccaatttctc tgcggagaat tatcagaaag agatttga                   828

<210> SEQ ID NO 34
<211> LENGTH: 618
<212> TYPE: DNA
<213> ORGANISM: Artificial Sequence
<220> FEATURE:
<223> OTHER INFORMATION: Description of Artificial Sequence:truncated or
      mutated ANT cDNA transgene ANTDNC3

<400> SEQUENCE: 34
atggcggctg cgaagaagaa gaggggacaa gaggatgttg tagttgttgg tcagaaacag       60
attgttcata gaaaatctat cgatactttt ggacaacgaa cttctcaata ccgaggcgtt      120
acaagacata gatggactgg tagatatgaa gctcatctat gggacaatag tttcaagaag      180
gaaggtcaca gtagaaaagg aagacaagtt tatctgggag gttatgatat ggaggagaaa      240
gctgctcgag catatgatct tgctgcactc aagtactggg gtccctctac tcacaccaat      300
ttctctgcgg agaattatca gaaagagatt gaagacatga gaacatgac tagacaagaa      360
```

```
tatgttgcac atttgagaag gaagagcagt ggtttctcta ggggtgcttc catctataga      420
ggagtcacaa gacatcacca gcatggaagg tggcaagcac ggattggtag agtcgctgga      480
aacaaagatc tctaccttgg aactttggaa acccaagaag aagctgcaga agcttacgat      540
gtagcagcaa ttaagttccg tggcacaaat gctgtgacta actttgatat cacgaggtac      600
gatgttgatc gtatctga                                                    618
```

```
<210> SEQ ID NO 35
<211> LENGTH: 333
<212> TYPE: DNA
<213> ORGANISM: Artificial Sequence
<220> FEATURE:
<223> OTHER INFORMATION: Description of Artificial Sequence:truncated or
      mutated ANT cDNA transgene ANTDNC4

<400> SEQUENCE: 35
atggcggctg cgaagaagaa gaggggacaa gaggatgttg tagttgttgg tcagaaacag       60
attgttcata gaaatctat cgatactttt ggacaacgaa cttctcaata ccgaggcgtt      120
acaagacata gatggactgg tagatatgaa gctcatctat gggacaatag tttcaagaag      180
gaaggtcaca gtagaaaagg aagacaagtt tatctgggag gttatgatat ggaggagaaa      240
gctgctcgag catatgatct tgctgcactc aagtactggg gtccctctac tcacaccaat      300
ttctctgcgg agaattatca gaaagagatt tga                                   333
```

```
<210> SEQ ID NO 36
<211> LENGTH: 525
<212> TYPE: DNA
<213> ORGANISM: Artificial Sequence
<220> FEATURE:
<223> OTHER INFORMATION: Description of Artificial Sequence:truncated or
      mutated ANT cDNA transgene ANTDNC5

<400> SEQUENCE: 36
atgcgaactt ctcaataccg aggcgttaca agacatagat ggactggtag atatgaagct       60
catctatggg acaatagttt caagaaggaa ggtcacagta gaaaaggaag acaagttat      120 ctgggaggtt atgatatgga ggagaaagct gctcgagcat atgatcttgc tgcactcaag      180
tactggggtc cctctactca caccaatttc tctgcggaga attatcagaa agagattgaa      240
gacatgaaga acatgactag acaagaatat gttgcacatt tgagaaggaa gagcagtggt      300
ttctctaggg gtgcttccat ctatagagga gtcacaagac atcaccagca tggaaggtgg      360
caagcacgga ttggtagagt cgctggaaac aaagatctct accttggaac ttttggaacc      420
caagaagaag ctgcagaagc ttacgatgta gcagcaatta agttccgtgg cacaaatgct      480
gtgactaact ttgatatcac gaggtacgat gttgatcgta tctga                      525
```

```
<210> SEQ ID NO 37
<211> LENGTH: 240
<212> TYPE: DNA
<213> ORGANISM: Artificial Sequence
<220> FEATURE:
<223> OTHER INFORMATION: Description of Artificial Sequence:truncated or
      mutated ANT cDNA ANTDNC6

<400> SEQUENCE: 37
atgcgaactt ctcaataccg aggcgttaca agacatagat ggactggtag atatgaagct       60
catctatggg acaatagttt caagaaggaa ggtcacagta gaaaaggaag acaagttat      120 ctgggaggtt atgatatgga ggagaaagct gctcgagcat atgatcttgc tgcactcaag      180
```
tactggggtc cctctactca caccaatttc tctgcggaga attatcagaa agagatttga        240

<210> SEQ ID NO 38
<211> LENGTH: 1668
<212> TYPE: DNA
<213> ORGANISM: Artificial Sequence
<220> FEATURE:
<223> OTHER INFORMATION: Description of Artificial Sequence:truncated or
      mutated ANT cDNA transgene ANTmNLS

<400> SEQUENCE: 38
atgaagtctt tttgtgataa tgatgataat aatcatagca acacgactaa tttgttaggg         60
ttctcattgt cttcaaatat gatgaaaatg ggaggtagag gaggtagaga agctatttac        120
tcatcttcaa cttcttcagc tgcaacttct tcttcttctg ttccacctca acttgttgtt        180
ggtgacaaca ctagcaactt tggtgtttgc tatggatcta acccaaatgg aggaatctat        240
tctcacatgt ctgtgatgcc actcagatct gatggttctc tttgcttaat ggaagctctc        300
aacagatctt ctcactcgaa tcaccatcaa gattcatctc caaggtggaa ggatttcttt        360
gggacccatc acaacaacac aagtcacaaa gaagccatgg atcttagctt agatagttta        420
ttctacaaca ccactcatga gcccaacacg actacaaact ttcaagagtt ctttagcttc        480
cctcaaacca gaaaccatga ggaagaaact agaaattacg ggaatgaccc tagtttgaca        540
catggagggt cttttaatgt agggtatat ggggaatttc aacagtcact gagcttatcc        600
atgagccctg ggtcacaatc tagctgcatc actggctctc accaccacca acaaaaccaa        660
aaccaaaacc accaaagcca aaaccaccag cagatctctg aagctcttgt ggagacaagc        720
gttgggtttg agacgacgac aatggcggct gcgagctcga cgagggggaca agaggatgtt        780
gtagttgttg gtcagaaaca gattgttcat agaaaatcta tcgatacttt tggacaacga        840
acttctcaat accgaggcgt tacaagacat agatggactg gtagatatga agctcatcta        900
tgggacaata gtttcaagaa ggaaggtcac agtagaaaag gaagacaagt ttatctggga        960
ggttatgata tggaggagaa agctgctcga gcatatgatc ttgctgcact caagtactgg       1020
ggtccctcta ctcacaccaa tttctctgcg gagaattatc agaaagagat tgaagacatg       1080
aagaacatga ctagacaaga atatgttgca catttgagaa ggaagagcag tggtttctct       1140
agggtgcttc catctatag aggagtcaca agacatcacc agcatggaag gtggcaagca       1200
cggattggta gagtcgctgg aaacaaagat ctctaccttg gaacttttgg aacccaagaa       1260
gaagctgcag aagcttacga tgtagcagca attaagttcc gtggcacaaa tgctgtgact       1320
aactttgata tcacgaggta cgatgttgat cgtatcatgt ctagtaacac actcttgtct       1380
ggagagttag cgcgaaggaa caacaacagc attgtcgtca ggaatactga agaccaaacc       1440
gctctaaatg ctgttgtgga aggtggttcc aacaaagaag tcagtactcc cgagagactc       1500
ttgagttttc cggcgatttt cgcgttgcct caagttaatc aaaagatgtt cggatcaaat       1560
atgggcggaa atatgagtcc ttggacatca acccctaatg ctgagcttaa gaccgtcgct       1620
cttactttgc ctcagatgcc ggttttcgct gcttgggctg attcttga                    1668

<210> SEQ ID NO 39
<211> LENGTH: 1668
<212> TYPE: DNA
<213> ORGANISM: Artificial Sequence
<220> FEATURE:
<223> OTHER INFORMATION: Description of Artificial Sequence:truncated or
      mutated ANT cDNA transgene ANTmRII, temperature
      sensitive mutant

```
<400> SEQUENCE: 39
atgaagtctt tttgtgataa tgatgataat aatcatagca acacgactaa tttgttaggg    60
ttctcattgt cttcaaatat gatgaaaatg ggaggtagag gagtagaga agctatttac   120 tcatcttcaa cttcttcagc tgcaacttct tcttcttctg ttccacctca acttgttgtt   180
ggtgacaaca ctagcaactt tggtgtttgc tatggatcta acccaaatgg aggaatctat   240
tctcacatgt ctgtgatgcc actcagatct gatggttctc tttgcttaat ggaagctctc   300
aacagatctt ctcactcgaa tcaccatcaa gattcatctc caaggtggaa ggatttcttt   360
gggacccatc acaacaacac aagtcacaaa gaagccatgg atcttagctt agatagttta   420
ttctacaaca ccactcatga gcccaacacg actacaaact ttcaagagtt ctttagcttc   480
cctcaaacca gaaccatgaa ggaagaaact agaaattacg ggaatgaccc tagtttgaca   540
catggagggt cttttaatgt aggggtatat ggggaatttc aacagtcact gagcttatcc   600
atgagccctg gtcacaatc tagctgcatc actggctctc accaccacca acaaaaccaa   660
aaccaaaacc accaaagcca aaccaccag cagatctctg aagctcttgt ggagacaagc   720
gttgggtttg agacgacgac aatggcggct gcgaagaaga gaggggaca gaggatgtt    780 gtagttgttg gtcagaaaca gattgttcat agaaaatcta tcgatacttt tggacaacga   840
acttctcaat accgaggcgt tacaagacat agatggactg gtagatatga agctcatcta   900
tgggacaata gtttcaagaa ggaaggtcac agtagaaaag gaagacaagt ttatctggga   960
ggttatgata tggaggagaa agctgctcga gcatatgatc ttgctgcact caagtactgg  1020
ggtccctcta ctcacaccaa tttctctgcg gagaattatc agaaagagat tgaagacatg  1080
aagaacatga ctagacaaga atatgttgca catttgagaa ggaagagcag tggtttctct  1140
agggtgcttc ccatctatag aggagtcaca agacatcacc agcatggaag gtggcaagca  1200
cggattggta gagtcgctgg aaacaaagat ctctaccta gcacttttgg aacccaagaa  1260
gaagctgcag aagcttacga tgtagcagca attaagttcc gtggcacaaa tgctgtgact  1320
aactttgata tcacgaggta cgatgttgat cgtatcatgt ctagtaacac actcttgtct  1380
ggagagttag cgcgaaggaa caacaacagc attgtcgtca ggaatactga agaccaaacc  1440
gctctaaatg ctgttgtgga aggtggttcc aacaaagaag tcagtactcc cgagagactc  1500
ttgagttttc cggcgatttt cgcgttgcct caagttaatc aaaagatgtt cggatcaaat  1560
atgggcggaa atatgagtcc ttggacatca aaccctaatg ctgagcttaa gaccgtcgct  1620
cttactttgc ctcagatgcc ggttttcgct gcttgggctg attcttga               1668

<210> SEQ ID NO 40
<211> LENGTH: 951
<212> TYPE: DNA
<213> ORGANISM: Artificial Sequence
<220> FEATURE:
<223> OTHER INFORMATION: Description of Artificial Sequence:novel
      chimeric ANT protein ANT-AP2sw1

<400> SEQUENCE: 40
atgacttctc aataccgagg cgttacaaga catagatgga ctggtagata tgaagctcat    60
ctatgggaca atagtttcaa gaaggaaggt cacagtagaa aaggaagaca agtttatctg   120
ggaggttatg atatggagga gaaagctgct cgagcatatg atcttgctgc actcaagtac   180
tggggtccct ctactcacac caatttctct gcggagaatt atcagaaaga gattgaagac   240
atgaagaaca tgactagaca agaatatgtt gcacatttga gaaggaagag cagtggtttc   300
```

-continued

| | |
|---|---|
| tctaggggtg cttccatcta tagaggagtc acaagacatc accagcatgg aaggtggcaa | 360 |
| gcacggattg gtagagtcgc tggaaacaaa gatctctacc ttggaactt tggaacccaa | 420 |
| gaagaagctg cagaagctta cgatgtagca gcaattaagt tccgtggcac aaatgctgtg | 480 |
| actaactttg atatcacgag gtacgatgtt gatcgtatca tgtcttcggt agggaatcct | 540 |
| actactccac aagatcacaa cctcgatctg agcttgggaa attcggctaa ttcgaagcat | 600 |
| aaaagtcaag atatgcggct caggatgaac caacaacaac aagattctct ccactctaat | 660 |
| gaagttcttg gattaggtca accggaatg cttaaccata ctcccaattc aaaccaccaa | 720 |
| tttccgggca gcagcaacat tggtagcgga ggcggattct cactgtttcc ggcggctgag | 780 |
| aaccaccggt ttgatggtcg ggcctcgacg aaccaagtgt tgacaaatgc tgcagcatca | 840 |
| tcaggattct ctcctcatca tcacaatcag atttttaatt ctacttctac tcctcatcaa | 900 |
| aattggctgc agacaaatgg cttccaacct cctctcatga gaccttcttg a | 951 |

<210> SEQ ID NO 41
<211> LENGTH: 795
<212> TYPE: DNA
<213> ORGANISM: Artificial Sequence
<220> FEATURE:
<223> OTHER INFORMATION: Description of Artificial Sequence:novel chimeric ANT protein ANT-AP2sw2

<400> SEQUENCE: 41

| | |
|---|---|
| atgtctcagt atagaggtgt tacgttttac cggcgtaccg gaagatggga atctcatatt | 60 |
| tgggactgtg ggaaacaagt ttacttaggt ggatttgaca ctgctcatgc agcagctcga | 120 |
| gcatatgata gagctgctat taaattccgt ggagtagaag cggatatcaa tttcaacatc | 180 |
| gacgattatg atgatgactt gaaacagatg actaatttaa ccaaggaaga gttcgtacac | 240 |
| gtacttcgcc gacaaagcac aggcttccct cgaggaagtt cgaagtatag aggtgtcact | 300 |
| ttgcataagt gtggtcgttg ggaagctcgt atgggtcaat tcttaggcaa aaagtatgtt | 360 |
| tatttgggtt tgttcgacac cgaggtcgaa gctgctagag cttacgataa agctgcaatc | 420 |
| aaatgtaacg gcaaagacgc cgtgaccaac tttgatccga gtatttacga tgaggaactc | 480 |
| aatgccgagt cgaacacact cttgtctgga gagttagcgc gaaggaacaa caacagcatt | 540 |
| gtcgtcagga atactgaaga ccaaaccgct ctaaatgctg ttgtggaagg tggttccaac | 600 |
| aaagaagtca gtactcccga gagactcttg agttttccgg cgattttcgc gttgcctcaa | 660 |
| gttaatcaaa agatgttcgg atcaaatatg ggcggaaata tgagtccttg gacatcaaac | 720 |
| cctaatgctg agcttaagac cgtcgctctt actttgcctc agatgccggt tttcgctgct | 780 |
| tgggctgatt cttga | 795 |

<210> SEQ ID NO 42
<211> LENGTH: 831
<212> TYPE: DNA
<213> ORGANISM: Artificial Sequence
<220> FEATURE:
<223> OTHER INFORMATION: Description of Artificial Sequence:novel chimeric ANT protein ANTdf1

<400> SEQUENCE: 42

| | |
|---|---|
| atgacttctc aataccgagg cgttacaaga catagatgga ctggtagata tgaagctcat | 60 |
| ctatgggaca atagtttcaa gaaggaaggt cacagtagaa aaggaagaca agtttatctg | 120 |
| ggaggttatg atatggagga gaaagctgct cgagcatatg atcttgctgc actcaagtac | 180 |
| tggggtcccct ctactcacac caatttctct gcggagaatt atcagaaaga gattgaagac | 240 |

-continued

```
atgaagaaca tgactagaca agaatatgtt gcacatttga gaaggaagag cagtggtttc    300 tctagggtg  cttccatcta tagaggagtc acaagacatc accagcatgg aaggtggcaa    360
gcacggattg gtagagtcgc tggaaacaaa gatctctacc ttggaacttt tggaacccaa    420
gaagaagctg cagaagctta cgatgtagca gcaattaagt tccgtggcac aaatgctgtg    480
actaactttg atatcacgag gtacgatgtt gatcgtatca tgtctagtaa cacactcttg    540
tctggagagt tagcgcgaag gaacaacaac agcattgtcg tcaggaatac tgaagaccaa    600
accgctctaa atgctgttgt ggaaggtggt tccaacaaag aagtcagtac tcccgagaga    660
ctcttgagtt ttccggcgat tttcgcgttg cctcaagtta atcaaaagat gttcggatca    720
aatatgggcg gaaatatgag tccttggaca tcaaacccta atgctgagct taagaccgtc    780
gctcttactt tgcctcagat gccggttttc gctgcttggg ctgattcttg a            831
```

METHODS FOR ALTERING ORGAN MASS IN PLANTS

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK.

Not Applicable

FIELD OF THE INVENTION

The present invention is directed to plant genetic engineering. In particular, it relates to methods of altering organ mass in plants through the modulation of plant growth and cell proliferation.

BACKGROUND OF THE INVENTION

Control of organ mass/size in plants is a significant goal in commercial agriculture. Plant shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (the mature ovary) and seedlings are the harvested product of numerous agronomically-important crop plants. Therefore the ability to manipulate the size/mass of these organs/structures through genetic control would be an important agricultural tool.

The intrinsic plant organ size is determined genetically, although it can be altered greatly by environment signals (e.g., growth conditions). In general, larger organs consist of larger numbers of cells. Since neither cell migration nor cell death plays a major role during plant development, the number of cells in plant organs depends on cell proliferation. Precise regulation of cell proliferation is also necessary for proper development of reproductive organs that make plants fertile. While some basic research has identified genes involved in plant organ development and fertility, little is known about genetic control of cell proliferation or its link to organogenesis including organ size/mass control and fertility in plants. Therefore an important goal is to understand the connection between genes that control organogenesis and genes that control cell proliferation. A great deal of basic research has shown that the components (e.g., cyclin dependent kinases, cyclins and their inhibitors) and mechanisms (e.g., regulation by phosphorylations, ubiquitin-mediated proteolysis) that control the cell cycle in yeast and animals are conserved in higher plants (Burssens et al., *Plant Physiol Biochem.*, 36:9–19 (1998)).

In *Arabidopsis*, the developing flower includes the ovule, the precursor of the seed. Wild-type ovule development in *Arabidopsis* has been extensively analyzed (Robinson-Beers et al., *Plant Cell*, 4:1237–1249 (1992); Modrusan et al., *Plant Cell*, 6:333–349 (1994) and Schneitz et al., *Plant J.*, 7:731–749 (1995)). A variety of mutations that affect ovule development have been identified (Klucher et al., *Plant Cell*, 8:137–153 (1996); Elliott et al., *Plant Cell*, 8:155–168 (1996); Baker et al., *Genetics.*, 145:1109–1124 (1997); Robinson-Beers et al., *Plant Cell.*, 4:1237–1249 (1992); Modrusan et al., *Plant Cell.*, 6:333–349 (1994); Ray, A., et al., *Proc Natl Acad Sci USA.*, 91:5761–5765 (1994); Lang, et al., *Genetics*, 137:1101–1110 (1994); Leon-Kloosterziel, *Plant Cell.*, 6:385–392 (1994); Gaiser et al., *Plant Cell*, 7:333–345 (1995)), and some of them have been found that specifically affect patterns of cell division (Schneitz et al., *Development*, 124:1367–1376 (1997)). Of those, several genes have been cloned; AINTEGUMENTA (ANT) (Klucher et al., *Plant Cell.*, 8:137–153 (1996); Elliott et al., *Plant Cell.*, 8:155–168 (1996)), AGAMOUS, (Yanofsky et al., *Nature*, 346:35–39 (1990); Bowman et al., *Plant Cell.*, 3:749–758 (1991)), SUPERMAN (Sakai et al., *Nature*, 378:199–203 (1995)). Because these genes are expressed and function not only in developing ovules but also in various developing organs, analysis of these mutations and genes has provided general information about the control of cell proliferation during plant development.

Another trait important to the manipulation of crop species is the ability to reproduce or propagate plants through asexual means, particularly vegetative propagation of sterile or hybrid plants, and regeneration of plants from transformed cells. Asexual reproduction includes regeneration of plants from cells or tissue, propagation of plants through cutting by inducing adventitious shoots and roots, and apomixis by forming somatic embryos. Asexual reproduction has the advantage that genetic clones of plants with desirable traits can be readily produced. Although asexual propagation of plants has been applied for improving agriculture for many years, not all plants can produce adventitious shoots or roots, or regenerate whole plants from cells or tissue.

In spite of the recent progress in defining the genetic control of plant cell proliferation, little progress has been reported in the identification and analysis of genes effecting agronomically important traits such as organ mass/size, fertility, asexual reproduction, and the like through regulating cell proliferation. Characterization of such genes would allow for the genetic engineering of plants with a variety of desirable traits. The present invention addresses these and other needs.

SUMMARY OF THE INVENTION

The present invention provides methods for modulating cell proliferation and thus cell number in plants by introducing into a plant an expression cassette containing a promoter operably linked to a nucleic acid encoding a modified ANT polypeptide. In some embodiments, the modified ANT polypeptides modulate organ mass or size in the plant without affecting fertility. Preferred polypeptides for this purpose include, for example, SEQ ID NO: 9–21 and 23–24. Also disclosed are methods of modulating cell proliferation using a temperature sensitive mutant of ANT (SEQ ID NO: 22).

Typically, the methods comprise modulating the expression of ANT in plants and selecting for fertile plants with altered size/mass. In some preferred embodiments, the ANT activity is increased and plants with increased cell proliferation and thus increased cell number are selected.

A variety of plant promoters can be used in the methods of the invention. The promoter can be constitutive, inducible or specific for an organ, tissue, or cell. In some embodiments a promoter from an ANT gene, e.g. SEQ ID NO: 3, or a promoter from an ANT ortholog is used. Expression of the ANT nucleic acids of the invention can be directed to any desired organ, tissue, or cell in the plant. In some preferred embodiments of the invention, the promoter directs expression of the ANT nucleic acid in shoot vegetative organs/ structures, such as leaf, stem and tuber. In other preferred embodiments, the promoter directs expression of the ANT nucleic acid in roots. In other preferred embodiments, the promoter directs expression of the ANT nucleic acid in flowers or floral organs/structures, such as bracts, sepals, petals, stamens, carpels, anthers and ovules. In different embodiments, the promoter directs expression of the ANT nucleic acid in seeds (e.g. embryo, endosperm, and seed coat) or fruits.

Definitions

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

The term "promoter" refers to regions or sequence located upstream and/or downstream from the start of transcription and which are involved in recognition and binding of RNA polymerase and other proteins to initiate transcription. A "plant promoter" is a promoter capable of initiating transcription in plant cells.

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

"Increased or enhanced ANT activity or expression of the ANT gene" refers to an augmented change in ANT activity. Examples of such increased activity or expression include the following. ANT activity or expression of the ANT gene is increased above the level of that in wild-type, non-transgenic control plants (i.e. the quantity of ANT activity or expression of the ANT gene is increased). ANT activity or expression of the ANT gene is in an organ, tissue or cell where it is not normally detected in wild-type, non-transgenic control plants (i.e. spatial distribution of ANT activity or expression of the ANT gene is increased). ANT activity or expression is increased when ANT activity or expression of the ANT gene is present in an organ, tissue or cell for a longer period than in a wild-type, non-transgenic controls (i.e., duration of ANT activity or expression of the ANT gene is increased).

As used herein, the term "asexual reproduction" refers to the formation of shoots, roots or a whole plant from a plant cell without fertilization. If the formation of the whole plant proceeds through a somatic embryo, the asexual reproduction can be referred to as apomixis.

The term "adventitious organ" and "adventitious shoot" refer to an organ (e.g., stem, leaf, or root) and a shoot arising in a place other than its usual site, respectively. For example, a root developing on a stem, or a shoot bud arising on a stem in a place other than the axil of a leaf. Adventitious organs or shoots may also arise in callus tissue in vitro. Such adventitious organs or shoots can then used to regenerate a whole plant using methods well known to those of skill in the art.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g., a genetically engineered coding sequence or an allele from a different ecotype or variety).

A polynucleotide "exogenous to" an individual plant is a polynucleotide which is introduced into the plant by any means other than by a sexual cross. Examples of means by which this can be accomplished are described below, and include *Agrobacterium*- mediated transformation, biolistic methods, electroporation, and the like. Such a plant containing the exogenous nucleic acid is referred to here as a $T_1$ (e.g., in *Arabidopsis* by vacuum infiltration) or $R_0$ (for plants regenerated from transformed cells in vitro) generation transgenic plant. Transgenic plants that arise from sexual cross or by selfing are descendants of such a plant.

An "ANT nucleic acid" or "ANT polynucleotide sequence" of the invention is a subsequence or full length polynucleotide sequence (SEQ ID NO: 1) which, encodes a polypeptide (SEQ ID NO: 2) and its complement, as described, for instance, by Klucher et al., *Plant Cell*, 8:137–153 (1996) and Elliott et al., *Plant Cell*, 8:155–168 (1996) (see, also, GenBank Accession Nos. U40256 and U41339). SEQ ID NO: 4, which encodes SEQ ID NO: 5, represents another "ANT nucleic acid" from Brassica. ANT gene products of the invention are characterized by the presence of an AP2 domain, first identified in AP2, this motif is characterized by a region of approximately 60–70 amino acid residues with a highly conserved core region with the capacity to form an amphipathic α-helix and/or to bind DNA (Jofuku et al., *Plant Cell*, 6:1211–1225 (1994); Ohme-Takagi and Shinshi, *Plant Cell*, 7: 173–182 (1995). The fill length ANT protein contains two AP2 domains (amino acids 281 to 357 and from 383 to 451 of SEQ ID NO: 2) and a linker region (amino acids 358 to 382), and the homology to other AP2 domain proteins is restricted to this region. An ANT polynucleotide of the invention typically comprises a coding sequence at least about 30–40 nucleotides to about 2500 nucleotides in length, usually less than about 3000 nucleotides in length. Usually the ANT nucleic acids of the invention are from about 100 to about 5000 nucleotides, often from about 500 to about 3000 nucleotides in length.

The term "truncated ANT nucleic acid" refers to a modified ANT nucleic acid, which contains the ANT-AP2 domain (amino acids 281–451) while lacking at least a portion of one or more of the following structural regions of the native ANT protein: 1) the first putative transcriptional activation domain (TA1, amino acids 13–53); 2) the second putative transcriptional activation domain (TA2, amino acids 214–231); 3) the potential nuclear localization site (NLS, amino acids 252–255); or 4) the C-terminal region (amino acids 452–555).

The term "modified ANT polypeptide" refers to a polypeptide that is encoded by a modified ANT nucleic acid. For example, a modified ANT polypeptide may be a truncated polypeptide which will consist essentially of an amino acid sequence of at least about 170 to about 190 residues (ANT-AP2 domain) and may be as long as about 500 residues. Usually the truncated ANT polypeptide will comprise an amino acid sequence of at least about 170 amino acid residues to about 300 amino acid residues. The modified ANT polypeptide may be a chimeric or fused protein which consists of the above portion of the ANT-AP2 domain and a portion of heterologous polypeptide originated from one or more foreign protein(s). The modified ANT polypeptides of the invention may comprise all or substantially all of the full length ANT protein but modified in such a way as to not affect fertility.

In the case of both expression of transgenes and inhibition of endogenous genes (e.g., by antisense, or co-suppression) one of skill will recognize that the inserted polynucleotide sequence need not be identical, but may be only "substantially identical" to a sequence of the gene from which it was derived. As explained below, these substantially identical variants are specifically covered by the term ANT nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "ANT nucleic acid", "ANT polynucleotide" and their equivalents. In addition, the terms specifically include those full-length and/or parts of the sequences substantially identical (determined as described below) with an ANT polynucleotide sequence and that encode proteins that retain the function of the ANT polypeptide (e.g., resulting from conservative substitutions of amino acids in the ANT polypeptide).

The term "altered fertility" includes any transient or permanent alteration of fecundity including inducing sterility as well as altered initiation of floral development (e.g., flowering time). Sterility can be caused, inter alia, by disruption of pollen development, dehiscence (i.e., male sterility), by disruption of ovule development (i.e., female sterility), or by disruption of pollination/fertilization processes caused by abnormal development of male/female organs (e.g., stigmatic papillae, transmitting tissue of septum). Flowering time is the developmental time or stage when a plant initiates and produces floral tissue.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.*, 4:11–17 (1988) e.g., as implemented in the program PC/GENE (Intelligenetics, Mountain View, Calif., USA).

The phrase "substantially identical," in the context of two nucleic acids or polypeptides, refers to a sequence or subsequence that has at least 25% sequence identity with a reference sequence. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 90%, 95%, or 99% compared to a reference sequence using the programs described herein; preferably BLAST using standard parameters, as described below. This definition also refers to the complement of a test sequence, when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.*, 2:482 (1981), by the homology alignment algorithm of Needleman & Wunsch, *J. Mol. Biol.*, 48:443 (1970), by the search for similarity method of Pearson & Lipman, *Proc. Nat'l Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.*, 35:351–360 (1987). The method used is similar to the method described by Higgins & Sharp, *CABIOS*, 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.*, 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA*, 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA*, 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising ANT nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

DESCRIPTION OF THE PREFERRED EMBODIMENTS

This invention relates to control of cell proliferation and thus cell number in plants by modulating ANT activity in plants. The present invention provides preferred modified ANT polynucleotides that can be used for this purpose. For example, in some embodiments, the polynucleotides of the invention encode modified ANT polypeptides that affect organ mass, but do not affect fertility in transgenic plants. In addition, the present invention provides temperature sensitive mutant ANT polypeptides that have nearly wild-type activity at low temperatures (e.g., 16° C.) but not at higher temperatures (e.g., 24° C.). Thus, the invention provides molecular strategies for manipulating plant biomass through controlling the number of cells and size/mass of plant shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (the mature ovary) and seedlings using ANT gene constructs. Thus, by regulating ANT expression transgenic plants with increased or decreased biomass can be produced. In yet other embodiments, formation of adventitious organs, shoots, or structures such as somatic embryos can be controlled using this method of the invention. Thus, the efficiency of asexual reproduction of plants, in particular reproduction of sterile or hybrid plants with desired traits and regeneration of transgenic plants from transformed tissue, can be improved.

Because the ANT gene product most likely functions as a transcription factor (Vergani et al., *FEBS Letters*, 400: 243–246 (1997)), one of skill will recognize that desired phenotypes associated with altered ANT activity can be obtained by modulating the expression or activity of ANT-regulated genes. Any of the methods described for increasing or decreasing ANT expression or activity can be used for this purpose.

Increasing ANT Activity or ANT Gene Expression

Any of a number of means well known in the art can be used to increase ANT activity in plants. Enhanced expression is useful, for example, to induce or enhance asexual reproduction, or increase organ size/mass in desired plant organs. Any organ can be targeted, such as plant shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit and seedlings. The beneficial effects of altering ANT activity need not be the direct result of increased cell proliferation. For instance, increased leaf size/mass will lead to an increase in photosynthesis, which will in turn lead to increased yield. Similarly increased mass/size of roots will lead to increased nutrient uptake and increased yield. Increased stem or pedicel thickness can be used to decreases losses due to breakage, e.g., in cereal crops and fruits.

Increasing Modified ANT Nucleic Acids of the Invention

Isolated sequences prepared as described herein can be used to introduce expression of a particular ANT nucleic acid to increase endogenous gene expression using methods well known to those of skill in the art. Preparation of suitable constructs and means for introducing them into plants are described below.

One of skill will recognize that the polypeptides encoded by the genes of the invention, like other proteins, have different domains that perform different functions. For example, the ANT protein has dual AP2 domains, two potential transcription activation domains, TA1 and TA2, a nuclear localization site in the N terminus, and a C terminus. Functional analysis of the different structural domains of the ANT protein has demonstrated that the AP2 domains of the ANT protein are responsible for the enlarged organ phenotype associated with the ANT protein but not for introducing male sterility in transgenic plants. For example, expression of a truncated ANT polypeptide containing the TA2 domain and the dual AP2 domains is sufficient for increasing organ size in plants whereas the C terminal region and the first 82 amino acids of the N terminal region are not required for increasing organ size upon ectopic expression in transgenic plants regardless of endogenous ANT function. With endogenous gene function, the N terminal region (amino acids 1–280) up to the first AP2 domain is not required for increasing organ size in plants.

Modified protein chains can also be readily designed utilizing various recombinant DNA techniques well known to those skilled in the art and described in detail, below. For example, the chains can vary from the naturally occurring sequence at the primary structure level by amino acid or polypeptide substitutions, additions, deletions, and the like. These modifications can be used in a number of combinations to produce the final modified protein chain, e.g, the expression of the ANT protein with a mutation of serine to glycine at amino acid 414 results in increased organ size in transgenic plants grown at 16° C. but not at 24° C.

Modification of Endogenous ANT Genes

Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used.

Alternatively, homologous recombination can be used to induce targeted gene modifications by specifically targeting the ANT gene in vivo (see, generally, Grewal and Klar, *Genetics*, 146:1221–1238 (1997) and Xu et al., *Genes Dev.*, 10:2411–2422 (1996)). Homologous recombination has been demonstrated in plants (Puchta et al., *Experientia*, 50:277–284 (1994), Swoboda et al., *EMBO J.*, 13:484–489 (1994); Offringa et al., *Proc. Natl. Acad. Sci. USA*, 90:7346–7350 (1993); and Kempin et al., *Nature*, 389: 802–803 (1997)).

In applying homologous recombination technology to the genes of the invention, mutations in selected portions of an ANT gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA*, 91:4303–4307 (1994); and Vaulont et al., *Transgenic Res.*, 4:247–255 (1995) are conveniently used to increase the efficiency of selecting for altered ANT gene expression in transgenic plants. The mutated gene will interact with the target wild-type gene in such a way that homologous recombination and targeted replacement of the wild-type gene will occur in transgenic plant cells, resulting in suppression of ANT activity.

Alternatively, oligonucleotides composed of a contiguous stretch of RNA and DNA residues in a duplex conformation with double hairpin caps on the ends can be used. The RNA/DNA sequence is designed to align with the sequence of the target ANT gene and to contain the desired nucleotide change. Introduction of the chimeric oligonucleotide on an extrachromosomal T-DNA plasmid results in efficient and specific ANT gene conversion directed by chimeric molecules in a small number of transformed plant cells. This method is described in Cole-Strauss et al., *Science*, 273: 1386–1389 (1996) and Yoon et al., *Proc. Natl. Acad. Sci. USA*, 93:2071–2076 (1996).

Other Means for Increasing ANT Activity

One method to increase ANT expression is to use "activation mutagenesis" (see, e.g., Hiyashi et al., *Science*, 258: 1350–1353 (1992)). In this method an endogenous ANT gene can be modified to be expressed constitutively, ectopically, or excessively by insertion of T-DNA sequences that contain strong/constitutive promoters upstream of the endogenous ANT gene. As explained below, preparation of transgenic plants overexpressing ANT can also be used to increase ANT expression. Activation mutagenesis of the endogenous ANT gene will give the same effect as overexpression of the transgenic ANT nucleic acid in transgenic plants. Alternatively, an endogenous gene encoding an enhancer of ANT activity or expression of the endogenous ANT gene can be modified to be expressed by insertion of T-DNA sequences in a similar manner and ANT activity can be increased.

Another strategy to increase ANT expression can be the use of dominant hyperactive mutants of ANT by expressing modified ANT transgenes. For example expression of modified ANT with a defective domain that is important for interaction with a negative regulator of ANT activity can be used to generate dominant hyperactive ANT proteins. Alternatively, expression of truncated ANT proteins which have only a domain that interacts with a negative regulator can titrate the negative regulator and thereby increase endogenous ANT activity. Use of dominant mutants to hyperactivate target genes is described in Mizukami et al., *Plant Cell*, 8:831–845 (1996).

Inhibition of ANT Activity or Gene Expression

As explained above, ANT activity is important in controlling a number of plant processes through the regulation of cell proliferation. Inhibition of ANT gene expression activity can be used, for instance, to decrease plant organ size/mass in plants. In particular, targeted expression of ANT nucleic acids that inhibit endogenous gene expression (e.g., antisense or co-suppression) can be used to inhibit ovule development at early stages and thus induce female sterility. The life span of the transgenic plants can therefore be extended because fertilization (seed formation) can activate and accelerate senescence processes of plants or organs.

Inhibition of ANT gene function can also be used to truncate vegetative growth, resulting in early flowering. Methods that control flowering time are extremely valuable in agriculture to optimize harvesting time as desired. Therefore, by regulating the function of the ANT genes in plants, it is possible to control time of flowering. For instance, acceleration of fertile plant growth can be obtained by expressing ANT antisense RNA during vegetative development to achieve early flowering. Expression of the ANT transgene can then be shut off during reproductive development to get fertile plants.

Inhibition of ANT Gene Expression

The nucleic acid sequences disclosed here can be used to design nucleic acids useful in a number of methods to inhibit ANT or related gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque, *Plant Sci. (Limerick)*, 105:125–149 (1995); Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. p. 181–238; Heiser et al., *Plant Sci. (Shannon)*, 127:61–69 (1997)) and by preventing the accumulation of mRNA which encodes the protein of interest, (see, Baulcombe, *Plant Mol. Bio.*, 32:79–88 (1996); Prins and Goldbach, *Arch. Virol.*, 141:2259–2276 (1996); Metzlaff et al., *Cell*, 88:845–854(1997), Sheehy et al., *Proc. Nat. Sci. USA*, 85:8805–8809(1988), and Hiatt et al., U.S. Pat. No. 4,801, 340).

The nucleic acid segment to be introduced generally will be substantially identical to at least a portion of the endogenous ANT gene or genes to be repressed. The sequence, however, need not be perfectly identical to inhibit expression. The vectors of the present invention can be designed such that the inhibitory effect applies to other genes within a family of genes exhibiting identity or substantial identity to the target gene. A nucleic acid segment or segments introduced into the regulatory region or regions of the ANT gene(s) can also be used for the inhibition of the expression of the endogenous ANT gene or genes.

For antisense suppression, the introduced sequence also need not be full length relative to either the primary transcription product or fully processed mRNA. Generally, higher identity can be used to compensate for the use of a shorter sequence. Furthermore, the introduced sequence need not have the same intron or exon pattern, and identity of non-coding segments may be equally effective. Normally, a sequence of between about 30 or 40 nucleotides and about full-length nucleotides should be used, though a sequence of at least about 100 nucleotides is preferred, a sequence of at least about 200 nucleotides is more preferred, and a sequence of about 500 to about 3500 nucleotides is especially preferred.

A number of gene regions can be targeted to suppress ANT gene expression. The targets can include, for instance, the coding regions, introns, sequences from exon/intron junctions, 5' or 3' untranslated regions, and the like.

Another well-known method of suppression is sense co-suppression. Introduction of nucleic acid configured in the sense orientation has been recently shown to be an effective means by which to block the transcription of target genes. For an example of the use of this method to modulate expression of endogenous genes (see, Assaad et al., *Plant Mol. Bio.*, 22:1067–1085 (1993); Flavell, *Proc. Natl. Acad. Sci. USA*, 91:3490–3496 (1994); Stam et al., *Annals Bot.*, 79:3–12 (1997); Napoli et al., *The Plant Cell*, 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting identity or substantial identity.

For co-suppression, the introduced sequence, needing less than absolute identity, also need not be full length, relative to either the primary transcription product or fully processed mRNA. This may be preferred to avoid concurrent production of some plants which are overexpressers. A higher identity in a shorter than full-length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using co-suppression technologies.

Oligonucleotide-based triple-helix formation can also be used to disrupt ANT gene expression. Triplex DNA can inhibit DNA transcription and replication, generate site-specific mutations, cleave DNA, and induce homologous recombination (see, e.g., Havre and Glazer, *J. Virology*, 67:7324–7331 (1993); Scanlon et al., *FASEB J.*, 9:1288–1296 (1995); Giovannangeli et al., *Biochemistry*, 35:10539–10548 (1996); Chan and Glazer, *J. Mol. Medicine* (*Berlin*), 75:267–282 (1997)). Triple helix DNAs can be used to target the same sequences identified for antisense regulation.

Catalytic RNA molecules or ribozymes can also be used to inhibit expression of ANT genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao and Pick, *Nature*, 365:448–451 (1993); Eastham and Ahlering, *J. Urology*, 156:1186–1188 (1996); Sokol and Murray, *Transgenic Res.*, 5:363–371 (1996); Sun et al., *Mol. Biotechnology*, 7:241–251 (1997); and Haseloff et al., *Nature*, 334:585–591 (1988).

Modification of Endogenous ANT Genes

Methods for introducing genetic mutations described above can also be used to select for plants with decreased ANT expression.

Other Means for Inhibiting ANT Activity

ANT activity may be modulated by eliminating the proteins that are required for ANT cell-specific gene expression. Thus, expression of regulatory proteins and/or the sequences that control ANT gene expression can be modulated using the methods described here.

Another strategy is to inhibit the ability of an ANT protein to interact with itself or with other proteins. This can be achieved, for instance, using antibodies specific to ANT. In this method cell-specific expression of ANT-specific antibodies is used to inactivate functional domains through antibody:antigen recognition (see, Hupp et al., *Cell*, 83:237–245 (1995)). Interference of activity of an ANT interacting protein(s) can be applied in a similar fashion. Alternatively, dominant negative mutants of ANT can be prepared by expressing a transgene that encodes a truncated ANT protein. Use of dominant negative mutants to inactivate target genes in transgenic plants is described in Mizukami et al., *Plant Cell*, 8:831–845 (1996).

Isolation of ANT Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998).

The isolation of ANT nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as flowers, and a cDNA library which contains the ANT gene transcript is prepared from the mRNA. Alternatively, cDNA may be prepared from mRNA extracted from other tissues in which ANT genes or homologs are expressed.

The cDNA or genomic library can then be screened using a probe based upon the sequence of a cloned ANT gene disclosed here. Probes may be used to hybridize with genomic DNA or cDNA sequences to isolate homologous genes in the same or different plant species. Alternatively, antibodies raised against an ANT polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the ANT genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see *PCR Protocols: A Guide to Methods and Applications*. (Innis, M, Gelfand, D., Sninsky, J. and White, T., eds.), Academic Press, San Diego (1990). Appropriate primers and probes for identifying ANT sequences from plant tissues are generated from comparisons of the sequences provided here (e.g. SEQ ID NO: 4) and those provided in Klucher et al. and Elliot et al., supra.

Polynucleotides may also be synthesized by well-known techniques as described in the technical literature. See, e.g., Carruthers et al., *Cold Spring Harbor Symp. Quant. Biol.*, 47:411–418 (1982), and Adams et al., *J. Am. Chem. Soc.*, 105:661 (1983). Double stranded DNA fragments may then be obtained either by synthesizing the complementary strand and annealing the strands together under appropriate conditions, or by adding the complementary strand using DNA polymerase with an appropriate primer sequence. Because at the very 5' and 3' ends the *Arabidopsis* ANT nucleotide sequence is very similar to the Brassica ANT nucleotide sequence but not to other *Arabidopsis* AP2-domain containing genes, the primers with nucleotide sequences shown in SEQ ID NO: 6, SEQ ID NO: 7, or SEQ ID NO: 8 can be used to screen/isolate ANT orthologs in different species by RT-PCR.

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al., *Ann. Rev. Genet.*, 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill. Such genes include for example, ACT11 from *Arabidopsis* (Huang et al., *Plant Mol. Biol.*, 33:125–139 (1996)), Cat3 from *Arabidopsis* (GenBank No. U43147, Zhong et al., *Mol. Gen. Genet.*, 251:196–203 (1996)), the gene encoding stearoyl-acyl carrier protein desaturase from *Brassica napus* (Genbank No. X74782, Solocombe et al., *Plant Physiol.*, 104:1167–1176 (1994)), GPc1 from maize (GenBank No. X15596, Martinez et al., *J. MoL Biol*, 208:551–565 (1989)), and Gpc2 from maize (GenBank No. U45855, Manjunath et al., *Plant Mol. Biol.*, 33:97–112 (1997)).

Alternatively, the plant promoter may direct expression of the ANT nucleic acid in a specific tissue, organ or cell type (i.e. tissue-specific promoters) or may be otherwise under more precise environmental or developmental control (i.e. inducible promoters). Examples of environmental conditions that may effect transcription by inducible promoters include anaerobic conditions, elevated temperature, the presence of light, or sprayed with chemicals/hormones. One of skill will recognize that a tissue-specific promoter may drive expression of operably linked sequences in tissues other than the target tissue. Thus, as used herein a tissue-specific promoter is one that drives expression preferentially in the target tissue or cell type, but may also lead to some expression in other tissues as well.

A number of tissue-specific promoters can also be used in the invention. For instance, promoters that direct expression of nucleic acids in flowers, ovules, or anthers (particularly the tapetum) are useful in methods in which sterility is desired. An example of a promoter that directs expression in the ovule is the promoter from the BEL1 gene described in Reiser et al., *Cell*, 83:735–742 (1995) (GenBank No. U39944). Examples of tapetal-specific promoters include TA29 from tobacco (Mariani et al., *Nature*, 347:737–41, (1990)), and A6 and A9 from Brassica (Paul et al., *Plant Mol. Biol.*, 19:611–22, (1992), Hird et al., *Plant Journal*, 4:1023–1033 (1993)). Anther-specific promoters could also be used such as ones isolated by Twell et al. (*Mol. Gen. Genet.*, 217:240–45, (1991)).

To introduce male sterility, the 2nd and 3rd floral organ (petal and stamens)—specific AP3 promoter (Day et al., *Development*, 121:2887, 1995), for example, can be used. The carpel specific AGL1 (Flanagan and Ma, *Plant J.*, 10:343, 1993) or AGL5 (Savidge, et al., *Plant Cell*, 7:721, 1995) promoter can be applied for inducing female sterility only. Sterile plants, yet with increased perianth organs, can be obtained by constitutively expressing the ANT gene through AG promoter (Sieburth and Meyerowitz, *Plant Cell*, 9:355, 1997) that is active only in reproductive organ primordia and developing male and female organs.

Using the AP1 promoter (Gustafson-Brown et al., *Cell*, 76:131, 1994) that is expressed in floral primordia at early stages of flower development and in developing perianth organs, fertile flowers with enlarged perianth organs can be produced. For the increase of aerial vegetative organ biomass, photosynthetic organ-specific promoters, such as the RBCS promoter (Khoudi et al., *Gene*, 197:343, 1997), can be used. Root biomass can be increased by the constitutive ANT expression under the control of the root-specific ANR1 promoter (Zhang & Forde, *Science*, 279:407, 1998). To increase seed size/mass (an agronomically import trait), seed-specific promoters, such as the LEC promoter (Lotan, et al., *Cell*, 93:1195 (1998)), the late-embroygenesis-abundant promoter (West et al., *Plant Cell*, 6:173 (1994)), beta-conglycininin alpha-subunit promoter (West et al.), the lectin promoter (Goldberg et al., *Science*, 266:605 (1994)), or the Kunitz trypsin inhibitor 3 promoter (Goldberg et al.) can be used. Any strong, constitutive promoters, such as the CaMV 35S promoter, can be used for the increase of total plant biomass.

If proper polypeptide expression is desired, a polyadenylation region at the 3'- end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

The present invention also provides promoter sequences from the ANT gene (SEQ ID NO: 3), which can be used to direct expression of the ANT coding sequence or heterologous sequences in desired tissues. ANT is expressed in meristematic cells throughout the plant. ANT promoter sequences of the invention are therefore useful in targeting expression to meristematic cells in lateral roots, leaf primordia, developing leaves, floral primordia, floral organ primordia, developing floral organs, ovule primordia, developing ovules, developing embryos, and vascular systems. Genes whose expression can be targeted to these cells in immature organs include disease resistance genes, such as the *Arabidopsis* NPR1 gene (Cao, et al., *Cell*, 88:57, 1997) and the nematode resistance locus Gro1 and the *Phytophthora infestans* resistance locus R7 of potato (Leister et al., *Nature Genetics*, 14:421, 1996), for increasing resistance to pathogens and insects in young, sensitive organs.

Because the ANT promoter is expressed in developing embryos at late stages, some genes encoding regulators or key enzymes for biosynthesis of storage oils, proteins, or starches, such as BiP (Hatano et al., *Plant and Cell Physiology*, 38:344, 1997), can be expressed by the control of the ANT promoter.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al., *Embo J.*, 3:2717–2722 (1984). Electroporation techniques are described in Fromm et al., *Proc. Natl. Acad. Sci. USA*, 82:5824 (1985). Ballistic transformation techniques are described in Klein et al., *Nature*, 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al., *Science*, 233:496–498 (1984), and Fraley et al., *Proc. Natl. Acad. Sci. USA*, 80:4803 (1983) and *Gene Transfer to Plants*, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplas*, pp. 21–73, CRC Press, Boca Raton, 1985. Regeneration can also be obtained from plant callus, explants, organs, or parts thereof. Such regeneration techniques are described generally in Klee et al., *Ann. Rev. of Plant Phys.*, 38:467–486 (1987).

The nucleic acids of the invention can be used to confer desired traits on essentially any plant. Thus, the invention has use over a broad range of plants, including species from the genera *Anacardium, Arachis, Asparagus, Atropa, Avena, Brassica, Chlamydomonas, Chlorella, Citrus, Citrullus, Capsicum, Carthamus, Cocos, Coffea, Cucumis, Cucurbita, Cyrtomium, Daucus, Elaeis, Fragaria, Glycine, Gossypium, Helianthus, Heterocallis, Hordeum, Hyoscyamus, Lactuca, Laminaria, Linum, Lolium, Lupinus, Lycopersicon, Macrocystis, Malus, Manihot, Majorana, Medicago, Nereocystis, Nicotiana, Olea, Oryza, Osmunda, Panieum, Pannesetum, Persea, Phaseolus, Pistachia, Pisum, Pyrus, Polypodium, Prunus, Pteridium, Raphanus, Ricinus, Secale, Senecio, Sinapis, Solanum, Sorghum, Theobromus, Trigonella, Triticum, Vicia, Vitis, Vigna*, and *Zea*.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of ANT mRNA or protein in transgenic plants. Means for detecting and quantitating mRNAs or proteins are well known in the art. The plants of the invention can also be identified by detecting the desired phenotype. For instance, increased biomass of organs or plants can be detected according to well-known techniques. Male or female sterility can be identified by testing for viable pollen and/or the ability to set seed.

The following Examples are offered by way of illustration, not limitation.

EXAMPLE 1

This example shows that increased ANT expression increases cell number and the size/mass of roots, leaves, floral organs, ovules and seeds in *Arabidopsis*.

An ANT cDNA with a BamHI site right before the initiation codon of the ANT coding nucleotide sequence was created by PCR using synthetic oligonucleotide primers. This ANT nucleic acid (from C at 268 to T at 2148 (1881 nucleotides) from SEQ ID NO: 1) was ligated at the BglII site of the plasmid vector pMON530 (Rogers, et al., *Meth. Enzymol.*, 153:253, 1987) under the constitutive 35S promoter, and the recombinant plasmid DNA which has an insert of the ANT cDNA in the sense direction with respect to the CaMV 35S promoter (35S::ANT) were selected. Agrobacterium cells were transformed with the recombinant plasmid DNA, and used for *Agrobacterium*-mediated plant transformation by vacuum infiltration with *Arabidopsis* plants (Col-0 ecotype). $T_1$ seeds were collected from transformed plants about three weeks after vacuum infiltration, and planted on MS plates with kanamycin for screening $T_1$ transgenic seedlings.

$T_1$ seeds include oversized seeds, which were distinguished because they did not pass through a mesh of defined size. The majority of these seeds were kanamycin resistant, carrying the 35S::ANT transgene. This phenotype was not observed in vector only controls.

Multiple $T_1$ seedlings were larger than vector only control transgenic seedlings. As they develop, $T_1$ plants produced a highly branched root system having a larger mass than vector only controls. In addition, the plants had enlarged leaves, floral organs, and ovules as compared to the vector only controls. For example, the average flower and leaf biomass of $T_1$ lines was approximately three times and 2.5 times that of the vector only control, respectively. DIC microscopy and scanning electron microscopy revealed that this enlarged organ phenotype of $T_1$ plants was due to the increased cell number in the organs. In addition, $T_1$ plants were sterile. Preliminary examination suggests that anthers fail to shed pollen (which are morphologically normal) and the ovules were unusually large with an increased number of nucellar cells that compress/displace the female gametophyte.

Because sterility made it difficult to generate and propagate homozygous transgenic lines, we used a chemical induction system as described by Aoyama, and Chua, *Plant J.*, 11:605–612 (1997) and McNellis et al., *Plant J.*, 14:247–257 (1998) to regulate ectopic ANT transcription. This system utilizes a chimeric transcription factor gene (35S::GVG), consisting of the 35S promoter, the DNA-binding domain of the yeast transcription factor GAL4, a transactivating domain, and the receptor domain of the glucocorticoid receptor (GR). The ANT gene was inserted downstream from a promoter (UAS::ANT) containing the binding site for the GVG transcription factor. The 35S::GVG/UAS::ANT construct was introduced into wild-type *Arabidopsis* and fertile transgenic lines were obtained generally as described above.

Transgenic $T_2$ plants were germinated on MS agar plates and transferred to plates either with or without the chemical inducer, dexamethasone (DEX), a synthetic glucocorticoid hormone that binds and activates the GVG transcription factor. Multiple transgenic lines were obtained that displayed an enlarged leaf phenotype after treatment with DEX. The increase in organ size/mass is due to an increased number of cells. DEX had no effect on control transgenic plants with only the 35S::GVG/UAS vector. Taken together, these results suggest that ectopic ANT expression increases organ size/mass by increasing cell number.

EXAMPLE 2

This example shows that essentially the same phenotypic changes observed in *Arabidopsis* were observed in tobacco.

For generating tobacco transgenic plants expressing ANT cDNA under the control of the constitutive 35S promoter, the above recombinant plasmid DNA was used for *Agrobacterium*-mediated tobacco callus transformation. Tobacco calli were induced from sterilized tobacco leaf (SR1 variety) placed on callus-inducing plates, then co-cultivated with Agrobacterium cells carrying the above recombinant DNA for three days. After washing bacterial cells out, leaf calli were placed on shoot-inducing agar plate containing kanamycin and carbenicillin to generate transformed shoots. These $R_0$ shoots were transferred on root inducing agar plates, then transplanted on soil after regeneration of roots. [deleted a sentence]

The $R_0$ plants in which the ANT gene was constitutively expressed under the control of the CaMV 35S promoter produced wider leaves (about 1.5 times that of vector only control transgenic plants), relatively larger flowers (about 1.7 time greater mass than vector only control transgenic plants), and sterility as observed with *Arabidopsis*. The sterility is largely caused by the failure of dehiscence of anthers as seen in the *Arabidopsis* transgenic anthers. Some $R_0$ plants produced functional pollen grains in their closed anthers, and produced seeds ($R_1$ seeds) upon self-pollination by hand using pollen grains dissected from the anther. These $R_1$ seeds had mass about 1.5 times that of seed from vector only control plants.

EXAMPLE 3

This example describes plant organ size/mass reduction and altered flowering by co-suppressing endogenous gene activity by the ANT transgene in *Arabidopsis* and tobacco.

*Arabidopsis* $T_1$ lines described above included lines exhibiting reduced organ size/mass and organ cell numbers. These plants were completely or partially female sterile, as are loss-of-function ant mutants. In these lines, expression of ANT mRNA was highly reduced, suggesting that co-suppression of the endogenous ANT gene, as well as that of the ANT cDNA, took place in the lines. From partially sterile $T_1$ lines, transgenic $T_2$ plants were obtained that segregated for the same co-suppressed phenotype as in $T_1$ parental plants. Reduction of organ size/mass was also observed in co-suppressed $R_0$ tobacco plants.

Multiple co-suppressed lines also exhibited early flowering. Plants of these lines displayed reduced numbers of rosette leaves and fewer days before bolting. Because early-flowering phenotype was not observed in loss-of-function ant mutants, co-suppression by the ANT transgene could also influence other unknown ANT related genes that regulate flowering time by itself or together with ANT. Similar results were also observed in co-suppressed transgenic tobacco plants.

EXAMPLE 4

This example shows that loss of ANT function reduces mature organ size by decreasing cell numbers.

Because ANT mRNA accumulated in leaf (Elliott et al., *Plant Cell*, 8:155–168 (1996)), we examined the effect of a loss-of-function ant mutation on vegetative shoot development. While there was no difference in the timing of leaf primordia initiation or the number of leaf primordia between ant-1 and control wild-type plants (not shown), the width and length of mature ant-1 leaves were both reduced in comparison with those of corresponding wild-type leaves. Because ant mutant floral organs were found to be reduced in size (Klucher et al., *Plant Cell*, 8:137–153 (1996); Elliott et al., *Plant Cell*, 8:155–168 (1996)), these observations demonstrate that loss of ANT function reduces organ size throughout shoot development.

A change in organ size can reflect an alteration in the size or number of cells, or both. To understand why ant-1 organs are smaller, we examined the size and number of cells in mature ant-1 organs and compared them with those in wild-type controls. The distal portion of the petal epidermis was observed initially because it has cells that are diploid and uniform in size and shape. We found that ant-1 organs had fewer cells per unit area and per organ than wild type, however ant-1 cells were much larger than normal. Essentially the same phenotype was observed in the epidermis and subdermal cell-layers of all ant-1 floral organs and leaves. Thus, systemic reduction in size of ant-1 organs is associated with a decrease in cell number, but not a decrease in cell size.

Because ant mutants reduce the number of floral organs, it has been suggested that ANT might be involved in organ primordium patterning as well as organ growth. To evaluate this possibility, we observed the pattern of sepal primordia in developing wild type and ant-1 floral buds under SEM. By the end of floral stage 4 (Smyth et al, *Plant Cell*, 2:755–767 (1990)), all four sepal primordia were initiated at the periphery of developing wild-type floral buds. In ant-1 floral buds at the comparable stage, the organ primordia initiated were arranged normally in ant-1 floral buds, although the number of floral organ was reduced (not shown). Thus, ANT appears to have little role in controlling the position of floral organ primordium in developing floral buds.

EXAMPLE 5

This example shows the isolation of an ANT ortholog from Brassica napus (Canola).

The nucleic acid sequence and the encoded protein of the Brassica cDNA are shown in SEQ ID NO: 4 and SEQ ID NO: 5 respectively.

To prepare this nucleic acid, total RNA was isolated from young shoot apices of Brassica napus (Canola) seedlings using TRIZOL as described by Colasanti et al., *Cell*, 93:593–603 (1998)). cDNA was made by reverse transcription, and amplified by PCR using the high fidelity thermotolerant DNA polymerase PFU and oligonucleotide primers. The primers had the initiation codon and the anti-parallel nucleotide sequence downstream of the stop codon of the *Arabidopsis* ANT nucleotide sequence, respectively. The PCR products were subcloned into an *E. coli* vector and screened by PCR using different sets of oligonucleotide primers having internal ANT nucleotide sequence. Nucleotide sequence of the inserted Brassica DNA of selected recombinant plasmid clones was determined and compared to the *Arabidopsis* ANT nucleotide sequence for confirmation. The Brassica ANT (BANT) gene shares 85.5% identity to the *Arabidopsis* ANT gene in their coding region at the nucleotide level and the BANT polypeptide sequence is 83.7% identical to the ANT polypeptide sequence, respectively.

EXAMPLE 6

This example shows use of the ANT 5'-upstream nucleotide sequence (promoter) for expressing heterologous genes in meristematic cells.

HindIII-BglII fragment which includes the correctly oriented ANT promoter was inserted into the pBI101 plasmid vector DNA (CLONTECH) at the HindIII and BamHI sites which are located right before the initiation codon of the GUS (beta-glucuronidase) gene. The same fragment was also inserted into the plasmid pBIN m-gfp5-ER (Haseloff, et al., *Proc. Natl. Acad. Sci. U.S.A.*, 94:2122–2127, (1997) at the HindIII-BamHI sites located immediately before the initiation codon of the GFP (green fluorescence protein) gene. *Arabidopsis* wild-type plants were transformed by these recombinant plasmids using the *Agrobacterium*- mediated vacuum infiltration method. Multiple $T_1$ lines, and their following generations, exhibited GUS activity or GFP expression in meristematic cells throughout plant development as expected, proving that the ANT promoter is useful for expressing a heterologous gene in meristematic cells.

EXAMPLE 7

This example shows activation of the cyclin D3 (CYCD3) gene expression by increasing ANT gene expression in *Arabidopsis* plants.

Cell proliferation is directly controlled by the activity of cell cycle regulatory genes, such as cyclins and cdks (Nasmyth, *Trends Genet.*, 12:405–412, (1996); Morgan, *Nature*, 374:131–134, 1995; and Burssens, et al., *Plant Physiol. Biochem.*, 36:9–19, (1998)). Because organs from $T_1$ transgenic lines in which ANT gene expression is controlled by the CaMV 35S promoter had increased number of cells, and thus increased cell proliferation activity, expression of cyclin genes in young and mature organs of $T_1$ plants was measured by quantitative RT-PCR analysis. In young developing organs, where cell proliferation was observed in both 35S::ANT and control plants, the difference of expression levels of cyclin genes between them were not significant. However, in mature organs, while mRNA accumulation of CYCD3, which encodes a key regulator for G1/S entry in the *Arabidopsis* cell cycle (Soni et al., *Plant Cell.*, 7:85–103 (1995); Fuerst et al., *Plant Physiol.*, 112:1023–1033 (1996), is no longer detected in control, it was detected in 35S::ANT lines. These results agree with observations that no growth differences were detected at early stages of organ development between 35S::ANT lines and control lines; however, when organs of control plants were mature and ceased cell proliferation, cells in the same aged organs of 35S::ANT plants continued to proliferate and give rise to enlarged organs as the result.

This result demonstrates that the increased constitutive ANT activity directly and/or indirectly controls the cell cycle machinery via regulating expression of a cell cycle regulator gene(s) and continuously activating cell proliferation in developing organs. This also indicates that certain genes involved in cell cycle machinery are targets of the ANT transcription factor gene (Klucher et al. and Elliot et al.). Taken together, these results suggest that modulation of expression of these ANT-target genes could regulate organ size/mass and fertility in plants.

EXAMPLE 8

This example shows that ectopic expression of BANT, an ANT ortholog from *Brassica napus* (Canola), increases organ mass/size in *Arabidopsis*.

The Brassica ANT (BANT) cDNA, which has the nucleic acid sequence shown in SEQ ID NO: 4, was inserted into the plasmid vector pMON530 (Rogers et al., *Method. Ezymol.*, 153:253, 1987) under the constitutive 35S promoter in the sense direction. The recombinant plasmid DNA was used for *Agrobacterium* transformation, and the *Agrobacterium* cells transformed with the 35S::BANT plasmid DNA was used for *Agrobacterium* mediated plant transformation by vacuum infiltration with *Arabidopsis* plants (Col-0 ecotype). $T_1$ seeds were collected about three weeks after vacuum infiltration, and planted on MS agar plates with kanamycin for screening $T_1$ transgenic seedlings.

$T_1$ plants ectopically expressing the 35S::BANT transgene exhibited multiple organ hyperplasia, as seen in 35S::ANT transgenic plants described above (Example 1). That is, leaves and floral organs were, at most, three times larger than control organs. These transgenic plants were essentially male sterile, and are often female sterile as well. Some plants, however, produced seeds upon fertilization with wild-type pollen grains by hand-pollination, and the $T_2$ seeds exhibited increased mass/size. The kanamycin-resistant $T_2$ seedlings developed into plants displaying the same phenotype as the $T_1$ plants, suggesting that the effect of ANT ectopic expression is heritable.

EXAMPLE 9

This example shows increased ANT expression induces asexual reproduction and formation of adventitious shoots, organs, and embryos in *Arabidopsis* plants.

Fully matured stems or organs, such as leaves, were dissected from $T_1$ plants ectopically expressing ANT and placed in water or on MS agar plates without any phytohormones. After about two-week incubation, adventitious root formation was observed at the cut surface of stems or leaves. Occasionally, adventitious roots were also produced from the leaf surface. This adventitious root formation was never observed control stems or leaves treated in the same way.

Excised inflorescence (flowering) stems from fully matured $T_1$ plants ectopically expressing ANT were placed on MS agar plates without phytohormones for 10 days. Adventitious root formation was observed in the cut surface of stems, while adventitious shoot formation was observed in the senesced floral buds. These shoots eventually produced roots as well, developing into complete plants that exhibited the same transgenic trait (enlarged organ size/mass) as the original plants. The control inflorescence stems did not show any activity of asexual reproduction under the same conditions.

Similar asexual reproduction was observed in embryos excised from developing 35S::ANT transgenic seeds. The late torpedo-stage to nearly mature embryos were excised from developing green seeds, and grew on phytohormone-free MS agar plates containing 50 μg/ml kanamycin. Although these embryos developed into seedlings, some cells reproduced secondary embryos or adventitious shoots, which also developed into complete plants. The control embryos did not propagate asexually under the same conditions.

EXAMPLE 10

This example shows that ectopic expression of structurally altered ANT proteins (ANTDN1, ANTDN2, ANTDN3, ANTDC1, ANTDNC1, ANTmNLS, and ANTmRII) increases organ size/mass in *Arabidopsis* plants.

Each cDNA encoding a structurally altered ANT protein was created by oligonucleotide-mediated in vitro mutagenesis. For N-terminal truncations, a new SalI site was introduced into an intact ANT cDNA at a position immediately before a desired, pre-existing ATG codon. As for C-terminal truncations or internal point mutations, a new termination codon or a codon(s) for altered amino acid(s) was introduced at the desired position. The SalI-BamHI fragment, which contains ANT cDNA with a 5' terminal deletion, or the BamHI fragment, containing either C-terminal truncated or internally point mutated ANT cDNA, was initially subcloned into the plasmid vector pGEM7zf. The altered ANT cDNA was subsequently cloned into the plant-binary plasmid vector pMON530 under the constitutive CaMV 35S promoter.

The recombinant plasmid DNA was used for Agrobacterium transformation. The transformed Agrobacterium cells were used for *Agrobacterium*- mediated transformation by vacuum infiltration with wild-type *Arabidopsis* plants (Col-0 ecotype). Transgenic *Arabidopsis* plants were screened by growth on Kanamycin containing MS agar plates and their phenotype was examined after transplantation and growth in soil.

Kanamycin resistant $T_1$ plants expressing ANTDN1, ANTDN2, ANTDN3, ANTDC1, ANTDNC1, ANTmNLS, ANTmRII, ANTsw1, or ANTdf1 cDNA exhibited the phenotype of increased organ size that was observed in plants ectopically expressing an intact ANT cDNA (Mizukami & Fischer, *Proc. Natl. Acad. Sci. USA*, 97:942–947 (2000)). The degree of organ size increase varied: on average, floral organ mass was approximately 1.5 to 2.2 times larger than non-transgenic plants grown under the same conditions. Enlarged vegetative organs were also observed in these transgenic plants. Further, our results demonstrate that both AP2 domains are required for ANT to yield increased organ size upon ectopic expression because none of the transgenic plants ectopically expressing a modified ANT lacking one of the AP2 domains produced enlarged organs.

EXAMPLE 11

This example describes plant organ size/mass reduction and altered flowering by the co-suppression of endogenous gene activity by the truncated or mutated ANT cDNA (transgene; ANTDN1, ANTDN2, ANTDN3, ANTDN4, ANTDC1, ANTDC2, ANTDNC1, ANTDNC2, ANTDNC3, ANTDNC4, ANTDNC5, ANTDNC6, ANTmNLS, or ANTmRII) in *Arabidopsis* plants.

*Arabidopsis* T1 lines (described in Example 10) included lines exhibiting reduced organ size/mass as previously observed in transgenic plants carrying an intact ANT transgene. These plants were completely or partially female sterile. In these lines, expression of ANT mRNA was greatly reduced, suggesting that co-suppression of the endogenous ANT gene, as well as that of the ANT cDNA, took place in the lines. From partially sterile T1 lines, as well as from crosses between sterile T1 lines and wild-type plants, transgenic T2 plants were obtained that segregated for the same co-suppressed phenotype as in T1 parental plants.

Multiple co-suppressed lines also exhibited the early-flowering phenotype. Plants of these lines displayed reduced numbers of rosette leaves and fewer days prior to bolting. Because the early-flowering phenotype was observed with transgenic plants carrying an intact ANT cDNA, the truncated or mutated ANT cDNA acts in the same fashion as the intact cDNA by causing early flowering, which was not observed in loss-of-function ant-1 mutants. Therefore, intact or modified ANT cDNA co-suppresses other unknown ANT-related gene(s) that regulate(s) flowering time independently or in conjunction with ANT.

EXAMPLE 12

This example shows that *Arabidopsis* plants ectopically expressing structurally altered ANT cDNA (ANTDN1, ANTDN2, ANTDN3, ANTDC1, or ANTDNC1) were not male infertile and displayed increases in organ size/mass. These plants also produced enlarged fruits and seeds by self-fertilization.

Our previous studies show that transgenic plants ectopically expressing ANT cDNA were male sterile (Mizukami & Fischer, *Proc. Natl. Acad. Sci. USA*, 97:942–947 (2000)). Although the above ANT cDNA encoding truncated or mutant ANT protein still functions in the same way by increasing organ size, plants expressing these ANT cDNA were fertile, as well as enlarged. This illustrates that these modified ANT cDNAs do not affect anther dehiscence, which is inhibited by ectopic expression of intact ANT cDNA and thereby results in male sterility.

These plants produced self-fertilized fruits (siliques) and seeds larger than those from non-transgenic control plants. The degree of fertility in the transgenic plants varied and there was no strict correlation between degrees of enlarged organ size and fertility. Further, the T2 plants obtained from self-fertilization displayed essentially the same phenotype as parental plants. These observations demonstrate that the ANT function in controlling organ size can be separated from its function in regulating male sterility through the modification of the transgene structure. Therefore, our results show that the N and/or C terminal regions of the AP2 domains are important for interacting with other protein(s) that control anther dehiscence, and that modification of these domains alters affinity of protein interactions, thereby suppressing male sterility in the transgenic plants.

EXAMPLE 13

This example shows that ectopic expression of novel chimeric ANT proteins (ANTsw1) containing the ANT-AP2 domains increased organ size/mass in *Arabidopsis* plants.

Each cDNA encoding novel chimeric ANT proteins was created by PCR using oligonucleotide primers. A NruI site followed by a new initiation codon, ATG were introduced immediately before the region encoding the first AP2 domain of ANT cDNA, and another NruI site was introduced at the end of the region encoding the second AP2 domain of the cDNA by PCR (ANT-AP2 fragment). Similarly, cDNA of ANT or AP2 (a gene encoding APETALA2, another AP2 domain transcription factor from *Arabidopsis*) including the C-terminal region was created and a new SnaBI or HpaI site and a BamHI site were introduced into the 5' end and 3' end of the cDNA, respectively, by PCR (ANT-C or AP2-C fragment). The 3' end of the ANT-AP2 fragment was ligated with the 5' end of the AP2-C or ANT-C fragment and the structure of the recombinant plasmid was confirmed by DNA sequencing. The fused ANT cDNA was then cloned into the plant-binary plasmid vector pMON530 under the constitutive CaMV 35S promoter.

The recombinant plasmid DNA was used for Agrobacterium transformation. The transformed Agrobacterium cells were used for *Agrobacterium*- mediated transformation by vacuum infiltration with wild-type *Arabidopsis* plants (Col-0 ecotype). Transgenic *Arabidopsis* plants were screened by growth on Kanamycin containing agar plates and their phenotype was examined.

Transgenic plants (T1 generation) expressing novel proteins of ANT-AP2 domains fused with either ANT-C region (i.e., ANTdf1) or AP2-C region (i.e., ANTsw1) exhibited enlarged floral phenotype. Because the amino acid sequence homology between ANT-C region and AP2-C region was less than 16%, it is not likely that AP2-C region functionally substituted for ANT-C region. Therefore, these results and those described in Example 1 demonstrate that the ANT-AP2 domains are sufficient for increasing organ size when the domains have additional homologous or heterologous polypeptide sequence, which stabilizes the protein and/or protein function.

EXAMPLE 14

This example demonstrates novel temperature-dependent activity of an ANT protein (ANTmRII), which has a mutation in the second AP2 domain. The alteration of Glycine to Serine at the amino acid 414 was made by in vitro mutagenesis using a mutant oligonucleotide. The ANT cDNA was subcloned into the pGEM7zf plasmid vector, and then cloned into pMON530 under the constitutive CaMV 35S promoter.

Agrobacterium cells were transformed and then used for *Agrobacterium*- mediated transformation by vacuum filtration with wild-type *Arabidopsis* plants (Col-0 ecotype). Kanamycin resistant transformants were screened by growth on MS-Kanamycin (50 mg/ml) agar plates, transferred to soil, and their phenotype determined. Initially, this was done at 24 C. Approximately 60% of total Kanamycin resistant T1 plants were like ant-1 mutants, whereby none of them exhibited the phenotype of male sterility with enlarged organs. Thus, ectopically expressed ANTmRII protein may act as a negative dominant factor for functional, endogenous ANT protein at 24 C. Alternatively, the modified transgenic ANT may co-suppress endogenous ANT gene expression at 24 C.

On the contrary, the transgenic T1 plants grown at 16 C exhibited the phenotype of enlarged organs and occasional male sterility. This indicates that ectopically expressed, modified ANT protein has nearly normal activity at 16 C. This demonstrates that ectopically expressed, modified ANT protein has nearly normal activity at 16 C. Therefore, the modified protein ANTmRII can be used for temporally controlling ANT function in transgenic plants via altering growth temperatures.

CONCLUSION

In higher plants intrinsic organ size is determined genetically, although it can be influenced greatly by environmental factors. The size of organs reflects the number and size of cells. The total cell number of an organ is determined by the proliferation of undifferentiated meristematic cells that are competent to divide. During shoot development, lateral organs are initiated as primordia from apical and lateral meristems. While most cells in organ primordia are meristematic and proliferate, cells lose meristematic competence and withdraw from the cell cycle as organs develop. Thus, the maintenance of meristematic competence of cells is a key mechanism that mediates organ growth and cell proliferation by defining total cell numbers, and thereby the size of plant organs. However, the molecular nature of meristematic competence and the developmental regulators that control meristematic competence are not well understood.

The *Arabidopsis* ANT gene encodes a transcription factor of the AP2-domain family that has been found only in plant systems. ANT mRNA accumulates in primordia of all lateral shoot organs and diminishes as organs develop. This suggests that ANT may have a general function in organ growth. Consistent with ANT expression in leaf primordia and undifferentiated growing leaves, it was found that all mature leaves of the loss-of-function ant-1 mutant were reduced in size in comparison with corresponding wild-type leaves. Because ant-1 floral organs were also smaller than normal, ANT is most likely required for organ growth throughout post-embryonic shoot development. Organ size can be influenced by cell size, cell number, or both. It was found that ant-1 organs had fewer cells per unit area and per organ than wild type, however ant-1 cells were much larger than normal. This demonstrates that the systemic reduction in size of ant-1 organs is the result of a decrease in cell number, but not a decrease in cell size. Therefore, ANT function is necessary to attain the intrinsic cell number of plant organs.

The experiments described here demonstrate that ectopic ANT expression is sufficient to increase organ size and mass by enhancing organ growth that is coordinated with organ morphogenesis in *Arabidopsis* plants. Differentiated cells in fully mature 35S::ANT petals were the same size as those in wild-type petals. Similarly, no obvious difference in cell size was detected in the epidermis between control and 35S::ANT organs other than petals. Thus, an increase of cell numbers, and not cell size, is primarily responsible for the enlarged 35S::ANT organs. Similar loss- and gain-of-function effects on organ size was observed when plants were grown plants grown under short-day, continuous-light conditions, and in poor or rich media. Thus, ANT function seems to be independent of the perception of external growth signals. In contrast to the striking effects on final organ size, ectopic ANT expression did not perceptibly alter the size or structure of apical and lateral meristems, nor did it change the size or number of organ primordia. Although loss of ANT function reduced the number of floral organs, the organ primordia initiated were arranged and sized normally in ant-1 floral buds. Therefore, ANT does not determine organ primordium size, and most likely does not influence organ primordium number by controlling the organization of the apical and lateral meristems.

How does ANT control cell numbers during organogenesis? In general, plant organ growth involves neither cell migration nor cell death; thus, organ cell number essentially depends on proliferation of the meristematic cells in developing organ. Because ANT is expressed in meristematic cells of the developing organs, it might modulate cell proliferation during organogenesis and thereby determine the total cell number in mature organs. To test this idea, the extent of cell proliferation in control and ant-1 organs was tested by measuring cell numbers and cell size of both developing and fully mature petals. During mid-floral stage 9, the adaxial epidermal cells of wild-type petals were not differentiated and divided frequently, whereas ant-1 petals had fewer undifferentiated cells than normal per unit area and per organ. This reduction in cell numbers became more pronounced in fully differentiated ant-1 petals at stage 15. Thus, there are fewer cell divisions than normal in ant-1 petals throughout organogenesis, particularly during later developmental stages prior to maturation. Cell growth occurred without cell division in ant-1 petals, resulting in extremely large cells.

These results suggest that ANT is required for the normal extent of cell proliferation, but not primarily for cell growth. To understand how ANT regulates the extent of cell proliferation, we studied how ectopic ANT expression affects organ size, cell size, and cell numbers during petal development. In contrast to the early effect on cell numbers in ant-1 petals, cell numbers and cell size in 35S::ANT petals at stage 9 were normal. This demonstrates that ectopic ANT expression does not increase cell growth or the frequency of cell proliferation in developing petals during early stages, and suggests that increased ANT activity does not alter the intrinsic cell cycle time. By stage 15, however, the total cell number of fully mature 35S::ANT petals reached approximately 2.5 times that of controls, indicating that additional cell divisions occurred in 35S::ANT petals prior to organ maturation, yet only after stage 9. Extra cell divisions must be coordinated with cell growth, since cell size in mature 35S::ANT petals is normal. Therefore, it is likely that ectopic ANT expression allows petal cells to proliferate for a longer period than normal without altering the intrinsic cell cycle time. Similar results were obtained when comparing growth of rosette leaves of 35S::ANT and control seedlings. At 16 days after germination (16 DAG), both 35S::ANT and control seedlings had the same number of rosette leaves, and all leaves of 35S::ANT seedlings were the same size as corresponding control leaves. However, 35S::ANT leaves continued to grow beyond the period in which corresponding control leaves ceased to grow, eventually giving rise to larger leaves than normal. This observation supports the hypothesis that prolonged cell proliferation coordinated with cell growth causes hyperplasia in 35S::ANT plants. Taken together, these observations suggests that ANT regulates the period of cell proliferation by maintaining meristematic competence of cells during organogenesis. The results presented here also suggest that ANT does not influence CycD3 expression in tissue where most cells are meristematic. Similar results were obtained in comparing mRNA levels of CycB1b (Cyc1bAt), a mitotic cyclin gene. Hence, ANT maintains the meristematic competence of cells, and consequently sustains expression of cell cycle regulators.

Another striking finding that connects ANT function with the maintenance of meristematic competence is neoplasia found in the *Arabidopsis* 35S::ANT organs. That is, clusters of undifferentiated cells (i.e., calli) were generated from wounds or senesced-surfaces of 35S::ANT plants, or detached-ends of fully differentiated 35S::ANT organs without external phytohormone treatment. These calli often differentiated into organs, such as roots, leaves, or shoots. This neoplasia was observed consistently in 35S::ANT organs, but never was seen in control organs treated in the same way. It is well established that differentiated plant tissue can induce calli after phytohormone treatment. Ectopic ANT expression in differentiated cells that are normally quiescent preserves meristematic competence and decreases their dependence on phytohormones for reentry into the cell cycle.

The findings presented here demonstrate that ANT is an intrinsic organ size regulator that influences organ growth and the period of cell proliferation during organogenesis. In a proposed model of ANT action in plant organ size regulation, developmental growth signals activate growth regulators, which positively regulate ANT during organogenesis. ANT functions to maintain meristematic competence of cells, thereby modulating the expression of cell cycle and cell growth regulators. As a result, ANT sustains cell proliferation that is coupled to cell growth in developing organs. Ectopically expressed ANT, therefore, results in the abnormal retention of meristematic competence of cells and causes hyperplasia and neoplasia, while the absence of ANT causes precocious termination of cell proliferation and organ growth. In plant and animal systems, growth signaling pathways and the cell cycle machinery appear to share many common factors. Nevertheless, given the immobile attributes of plant life and plant cells, which are surrounded by rigid cell walls, some aspects of plant growth and cell proliferation are likely to be regulated and coordinated in a different way from those of animals. Thus, it may not be surprising that ANT is a plant specific regulator, and identification of upstream regulators and downstream targets of ANT may reveal how plants uniquely coordinate cell proliferation with pattern formation to control organ size. It has been suggested that the genetic basis for plant interspecies diversity of phenotype might be minor changes in the structure or expression of orthologous regulatory genes. Hence, differences in structure and expression pattern of ANT and its orthologs, at least in part, may be a mechanism that is responsible for the interspecies diversity of organ size in higher plants. Finally, increasing organ mass by ectopic ANT expression might be a new method for improving the yield of agriculturally important plants.

As previously mentioned, ANT encodes a putative transcription factor of the AP2 family, which contains dual AP2 domain, a double repeat of a characteristic sequence of approximately 70 amino acids. The ANT protein also has two potential transcription activation domains, TA1 and TA2, and a deduced nuclear localization site (NLS) in N-terminus to the dual AP2 domain, whereas its C-terminus shows no significant structural similarity to any known functional domains, or proteins including APETALA2 (AP2), another AP2 family protein. To examine in planta function of the structural domains of the ANT protein, 18 modified 35S::ANT cDNA clones encoding modifed ANT proteins were generated, e.g., truncated, mutant, and chimeric ANT proteins, and phenotypes of transgenic plants expressing them were analyzed. It was demonstrated that expression of part of the ANT protein containing TA2 and the dual AP2 domain is sufficient for increasing organ size in both wild-type and ant-deficient mutant background, whereas ectopic expression of the dual AP2 domain of the ANT protein fused with a C-terminal region of either ANT or AP2 protein is adequate to make organ larger than normal when endogenous ANT is functional. These results indicate that the dual AP2 domain is responsible for ANT function in plant organ size control and may contributes to protein-protein interaction as well as binding to the target DNA in plants. In contrast, TA1 as well as NLS appeared dispensable and their functions, if they have any, are most likely redundant. It was further demonstrated that male sterility, another phenotype associated with gain of ANT function, can be eliminated from transgenic plants with large organs by expressing modified ANT cDNA. Thus, transgenes expressing modified ANT proteins, as well as those expressing intact ANT proteins would be useful for altering plant organ size and fertility to improve the yield of agriculturally important plants.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method of increasing cell proliferation in a plant, the method comprising introducing into the plant an expression cassette containing a plant promoter operably linked to an ANT nucleic acid encoding a truncated ANT polypeptide having no more than about 500 amino acids, said truncated ANT polypeptide comprising the amino acid sequence of positions 281–451 of SEQ ID NO:2; and selecting plants with increased size or mass when compared to a wild-type plant.

2. The method of claim 1, wherein the truncated ANT polypeptide comprises a sequence as shown in SEQ ID NO:13.

3. The method of claim 1, wherein the plant has increased floral organ mass.

4. The method of claim 1, wherein the plant has increased vegetative organ mass.

5. The method of claim 1, wherein the step of introducing is carried out using *Agrobacterium*.

6. The method of claim 1, wherein the promoter is heterologous to the ANT nucleic acid encoding the truncated ANT polypeptide.

7. The method of claim 6, wherein the promoter is a constitutive promoter.

8. The method of claim 7, wherein the promoter is CaMV 35S promoter.

9. The method of claim 6, wherein the promoter is a tissue specific promoter.

10. The method of claim 1, wherein the plant is *Arabidopsis*.

11. A recombinant expression cassette comprising plant promoter operably linked to an ANT nucleic acid encoding a truncated ANT polypeptide having no more than about 500 amino acids, said truncated ANT polypeptide comprising the amino acid sequence of positions 281–451 of SEQ ID NO:2.

12. The recombinant expression cassette of claim 11, wherein the promoter is heterologous to the ANT nucleic acid encoding the truncated ANT polypeptide.

13. The recombinant expression cassette of claim 12, wherein the promoter is a constitutive promoter.

14. The recombinant expression cassette of claim 13, wherein the promoter is CaMV 35S promoter.

15. The recombinant expression cassette of claim 12, wherein the promoter is a tissue specific promoter.

16. The recombinant expression cassette of claim 11, wherein the truncated ANT polypeptide comprises a sequence as shown in SEQ ID NO:13.

17. The method of claim 1, wherein the truncated ANT polypeptide comprises a sequence as shown in SEQ ID NO:9.

18. The method of claim 1, wherein the truncated ANT polypeptide comprises a sequence as shown in SEQ ID NO:10.

19. The recombinant expression cassette of claim 11, wherein the truncated ANT polypeptide comprises a sequence as shown in SEQ ID NO:9.

20. The recombinant expression cassette of claim 11, wherein the truncated ANT polypeptide comprises a sequence as shown in SEQ ID NO:10.

21. The method of claim 1, wherein the truncated ANT polypeptide comprises a sequence as shown in SEQ ID NO:11.

22. The method of claim 1, wherein the truncated ANT polypeptide comprises a sequence as shown in SEQ ID NO:15.

23. The recombinant expression cassette of claim 11, wherein the truncated ANT polyprptide comprises a sequence as shown in NO:11.

24. The recombinant expression cassette of claim 11, wherein the truncated ANT polypeptide comprises a sequence as shown in SEQ ID NO:15.

* * * * *